US007838678B2

(12) United States Patent
Kim et al.

(10) Patent No.: US 7,838,678 B2
(45) Date of Patent: Nov. 23, 2010

(54) PROCESS FOR PREPARING ATAZANAVIR BISULFATE AND NOVEL FORMS

(75) Inventors: Soojin Kim, Demarest, NJ (US); Bruce T. Lotz, Yardville, NJ (US); Mary F. Malley, Lawrenceville, NJ (US); Jack Z. Gougoutas, Princeton, NJ (US); Martha Davidovich, East Brunswick, NJ (US); Sushil K. Srivastava, Dayton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/360,468

(22) Filed: Jan. 27, 2009

(65) Prior Publication Data

US 2009/0203630 A1 Aug. 13, 2009

Related U.S. Application Data

(62) Division of application No. 11/119,558, filed on May 2, 2005.

(60) Provisional application No. 60/568,043, filed on May 4, 2004, provisional application No. 60/607,533, filed on Sep. 7, 2004.

(51) Int. Cl.
C07D 213/56 (2006.01)
(52) U.S. Cl. ..................................... 546/332
(58) Field of Classification Search ................. 546/332; 514/357
See application file for complete search history.

(56) References Cited

U.S. PATENT DOCUMENTS

| 3,980,637 A | 9/1976 | Grossman et al. |
| 4,022,776 A | 5/1977 | Nakagawa et al. |
| 4,800,084 A | 1/1989 | Zerbe |
| 4,847,265 A | 7/1989 | Badorc et al. |
| 5,158,777 A | 10/1992 | Abramowitz et al. |
| 5,428,048 A | 6/1995 | Malamas et al. |
| 5,489,436 A | 2/1996 | Hoy et al. |
| 5,541,205 A | 7/1996 | Malamas et al. |
| 5,849,911 A | 12/1998 | Fässler et al. |
| 6,086,919 A | 7/2000 | Bauer et al. |
| 6,087,383 A * | 7/2000 | Singh et al. ................. 514/357 |
| 6,136,345 A | 10/2000 | Grimmett et al. |
| 6,316,438 B1 | 11/2001 | Yu et al. |
| 6,395,767 B2 | 5/2002 | Robl et al. |
| 6,414,002 B1 | 7/2002 | Cheng et al. |
| 6,653,314 B2 | 11/2003 | Cheng et al. |
| 6,670,344 B2 | 12/2003 | Venit et al. |
| 6,727,271 B2 | 4/2004 | Cheng et al. |
| 6,753,012 B2 | 6/2004 | Cappola |
| 2002/0094992 A1 | 7/2002 | MacLean |
| 2004/0022855 A1 | 2/2004 | Yoon et al. |
| 2005/0214373 A1 | 9/2005 | Desai et al. |
| 2005/0256314 A1 | 11/2005 | Kim et al. |
| 2005/0266080 A1 | 12/2005 | Desai et al. |
| 2005/0288343 A1 | 12/2005 | Rusowicz et al. |

FOREIGN PATENT DOCUMENTS

| EP | 1 186 293 | 3/2002 |
| EP | 1 243 266 | 9/2002 |
| WO | WO 01/52825 | 7/2001 |
| WO | WO 02/085335 | 10/2002 |

OTHER PUBLICATIONS

Goldstein, S.W. et al., "Hydroxyurea Derivatives as Hypoglycemic Agents", J, Med. Chem., vol. 36, No. 15, pp. 2238-2240 (1993).
Malamas, M.S. at al., "Azole Phenoxy Hydroxyureas as Selective and Orally Active inhibitors of 5-Lipoxygenase", J. Med. Chem., vol. 39, No. 1, pp. 237-245 (1996).
U.S. Appl. No. 11/119,551, filed May 2, 2005, Kim et al.
Earl, W.L. et al., "Measurement of $^{13}$C Chemical Shifts in Solids", Journal of Magnetic Resonance, vol. 48, pp. 35-54 (1982).
Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-734 (1997).
Jones, A.G. et al., "Programmed Cooling Crystallization of Potassium Sulphate Solutions", Chemical Engineering Science, vol. 29, pp. 105-118 (1974).
Metz, G. et al., "Ramped-Amplitude Cross Polarization in Magic-Angle-Spinning NMR", Journal of Magnetic Resonance, Series A, vol. 110, pp. 219-227 (1994).
Mullin, J.W. et al., "Programmed cooling of batch crystallizers", Chemical Engineering Science, vol. 26, pp. 369-377 (1971).
Otwinowski, Z. et al., "Processing of X-Ray Diffraction Data Collected in Oscillation Mode", Macromolecular Crystallography, Part A, Methods in Enzymology, vol. 276, Academic Press, publ., Carter, Jr., C.W. et al., eds., pp. 307-326 (1997).
Xu, Z. et al., "Process Research and Development for an Efficient Synthesis of the HIV Protease Inhibitor BMS-232632", Organic Process Research & Development, vol. 6, No. 3, pp. 323-328 (2002).
Yin, S. et al., "Simulated PXRD Patterns in Studies of the Phase Composition and Thermal Behavior of Bulk Crystalline Solids", American Pharmaceutical Review, vol. 6, No. 2, pp. 80-85 (2003).

* cited by examiner

*Primary Examiner*—Shailendra Kumar
(74) *Attorney, Agent, or Firm*—Burton Rodney

(57) ABSTRACT

A process is provided for preparing the HIV protease inhibitor atazanavir bisulfate wherein a solution of atazanavir free base is reacted with concentrated sulfuric acid in an amount to react with less than about 15% by weight of the free base, seeds of Form A crystals of atazanavir bisulfate are added to the reaction mixture, and as crystals of the bisulfate form, additional concentrated sulfuric acid is added in multiple stages at increasing rates according to a cubic equation, to effect formation of Form A crystals of atazanavir bisulfate.

A process is also provided for preparing atazanavir bisulfate as Pattern C material. A novel form of atazanavir bisulfate is also provided which is Form E3 which is a highly crystalline triethanolate solvate of the bisulfate salt from ethanol.

12 Claims, 11 Drawing Sheets

Carbon-13 SSNMR of Form A

PROCESS FOR PREPARING ATAZANAVIR BISULFATE AND NOVEL FORMS

REFERENCE TO OTHER APPLICATIONS

This application is a divisional of U.S. patent application Ser. No. 11/119,558, filed May 2, 2005, that claims the benefit of U.S. Provisional Application Nos. 60/568,043, filed May 4, 2004, and 60/607,533, filed Sep. 7, 2004, the disclosures of which are incorporated herein by reference.

FIELD OF THE INVENTION

The present invention relates to a process for preparing the HIV protease inhibitor atazanavir bisulfate and novel forms thereof.

BACKGROUND OF THE INVENTION

U.S. Pat. No. 5,849,911 to Fässler et al. discloses a series of azapeptide HIV protease inhibitors (which includes atazanavir) which have the structure

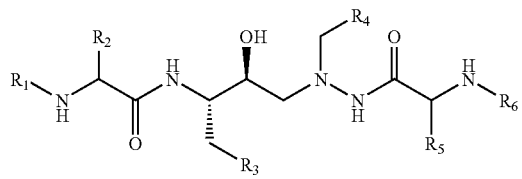

wherein $R_1$ is lower alkoxycarbonyl, $R_2$ is secondary or tertiary lower alkyl or lower alkylthio-lower alkyl, $R_3$ is phenyl that is unsubstituted or substituted by one or more lower alkoxy radicals, or $C_4$-$C_8$ cycloalkyl, $R_4$ is phenyl or cyclohexyl each substituted in the 4-position by unsaturated heterocyclyl that is bonded by way of a ring carbon atom, has from 5 to 8 ring atoms, contains from 1 to 4 hetero atoms selected from nitrogen, oxygen, sulfur, sulfinyl (—SO—) and sulfonyl (—$SO_2$—) and is unsubstituted or substituted by lower alkyl or by phenyl-lower alkyl, $R_5$, independently of $R_2$, has one of the meanings mentioned for $R_2$, and $R_6$, independently of $R_1$, is lower alkoxycarbonyl, or a salt thereof, provided that at least one salt-forming group is present which includes various pharmaceutically acceptable acid addition salts thereof.

Several methods for preparing the azapeptides are provided including preparation of a compound where $R_1$ and $R_6$, and $R_2$ and $R_5$ are in each case two identical radicals, wherein a diamino compound of the structure

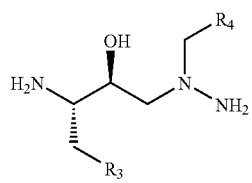

(a)

is condensed with an acid of the structure

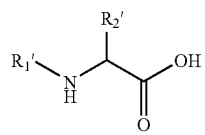

(b)

or with a reactive acid derivative thereof, wherein $R_1'$ and $R_2'$ are as defined for $R_1$ and $R_6$, and for $R_2$ and $R_5$, respectively.

In forming atazanavir employing the above method the diamino compound (a) which will have the structure

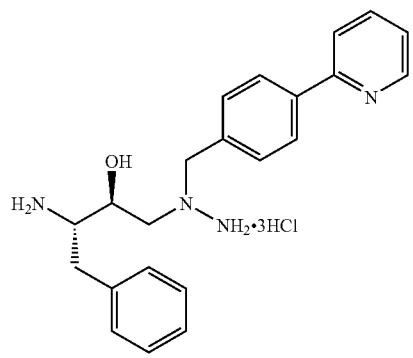

is prepared by coupling the epoxide

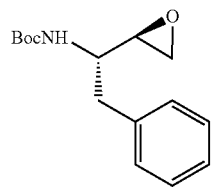

with a hyrazinocarbamate

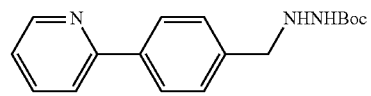

in the presence of isopropyl alcohol to form the protected diamine

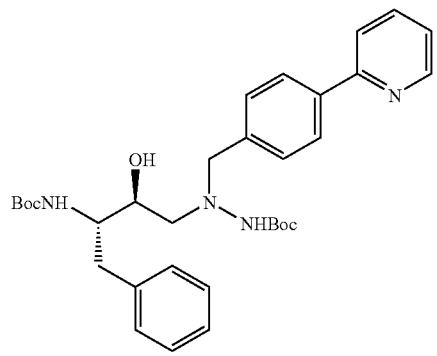

which is treated with hydrochloric acid in the presence a solvent such as tetrahydro-furan to form the diamine (a)

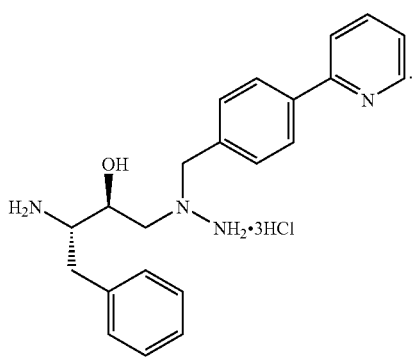

(a)

The diamine is isolated and used in the next coupling step where it is reacted with an acid (b)

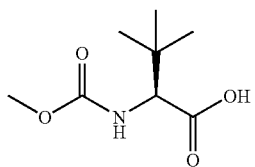

(b)

or a reactive ester thereof employing a coupling agent such as O-(1,2-dihydro-2-oxo-1-pyridyl)-N,N,N¹N¹-tetramethyluronium-tetrafluoro-borate (TPTU).

It has been found that the diamine free base is unstable and therefore undesirable for use in preparing the free base of atazanavir.

U.S. Pat. No. 6,087,383 to Singh et al. discloses the bisulfate salt of the azapeptide HIV protease inhibitor known as atazanavir which has the structure

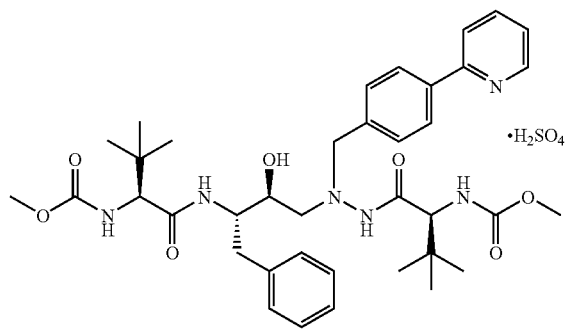

(also referred to as atazanavir bisulfate or atazanavir sulfate).

Example 3 of Singh et al. describes the preparation of atazanavir bisulfate in the form of Type-II crystals which are a hydrated hygroscopic and crystalline form and Type-I crystals which appear to be an anhydrous/desolvated crystalline form.

BRIEF DESCRIPTION OF THE INVENTION

In accordance with the present invention, novel forms of atazanavir bisulfate are provided which includes Pattern C material and Form E3. Pattern C material is preferred.

In addition, in accordance with the present invention, a process is provided for preparing atazanavir bisulfate in the form of Form A crystals (bulk drug) (which are referred to as Type I crystals in Example 3 of U.S. Pat. No. 6,087,383 to Singh et al). The Form A crystals prepared by the process of the invention have a desired substantially consistent particle size distribution and substantially consistent mean particle size, and are employed in the conversion to Pattern C material, a partially crystalline material, which is formulated with various excipients to prepare the drug product.

The process of the invention for preparing Form A crystals of atazanavir bisulfate salt employs a modified cubic crystallization technique wherein sulfuric acid is added at an increasing rate according to a cubic equation (as described hereinafter), and includes the steps of reacting a solution of atazanavir free base in an organic solvent (in which the atazanavir bisulfate salt is substantially insoluble) with a first portion of concentrated sulfuric acid in an amount to react with less than about 15%, preferably less than about 12%, by weight of the atazanavir free base, adding seeds of atazanavir bisulfate Form A crystals to the reaction mixture, and as crystals of atazanavir bisulfate form, adding additional concentrated sulfuric acid in multiple stages at increasing rates according to a cubic equation to effect formation of Form A crystals.

In addition, in accordance with the present invention, a process is provided for preparing a form of atazanavir which is derived from and includes atazanavir bisulfate, and which is referred to as Pattern C material. Pattern C may be produced by suspending crystals of Form A in water and drying. Alternatively, Pattern C material may be formed by subjecting crystals of Form A to high relative humidity of greater than about 95% RH (water vapor) for at least 24 hours. Pattern C material may also be formed by wet granulating the atazanavir bisulfate or a combination of atazanavir bisulfate and excipients and drying the wet granulation.

In a preferred embodiment, Form A crystals are mixed with formulating excipients such as one or more bulking agents, for example lactose, one or more disintegrants, such as crospovidone, and wet granulated to directly form Pattern C material in admixture with the excipients.

Further in accordance with the present invention, a new form of atazanavir bisulfate is provided, namely, Form E3 which is a highly crystalline form of the triethanolate solvate of atazanavir bisulfate.

Form E3 is prepared by slurrying atazanavir free base in ethanol, treating the slurry with concentrated sulfuric acid, heating and seeding the resulting solution with ethanol wet E3 crystals, treating the mixture with heptane (or other solvent such as toluene or hexane), filtering and drying.

Still further in accordance with the present invention, a process is provided for preparing Form A crystals of atazanavir bisulfate which includes the steps of preparing a triamine salt of the structure

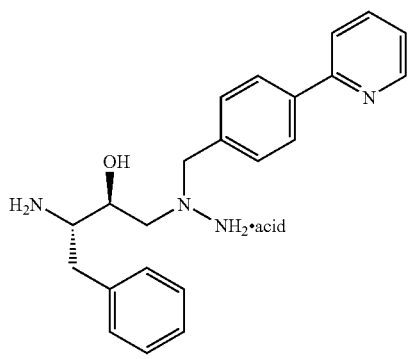

preferably the HCl (3 moles) salt) and without isolating the triamine salt, reacting the triamine salt with an active ester, preferably of the structure

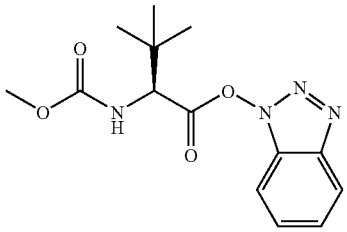

in the presence of a base and organic solvent to form atazanavir free base which, without isolating, is converted to the atazanavir bisulfate via a modified cubic crystallization technique as described herein.

In addition, in accordance with the present invention, a novel atazanavir bisulfate composition is provided which includes atazanavir bisulfate as Form A crystals or Pattern C material, and a pharmaceutically acceptable carrier therefor. The pharmaceutically acceptable carrier may include fillers, binders, disintegrants, lubricants, and other conventional excipients.

The various forms of atazanavir bisulfate according to the invention may be characterized using various techniques, the operation of which are well known to those of ordinary skill in the art. The forms may be characterized and distinguished using single crystal X-ray diffraction, which is based on unit cell measurements of a single crystal of a form at a fixed analytical temperature. A detailed description of unit cells is provided in Stout & Jensen, X-Ray Structure Determination: A Practical Guide, Macmillan Co., New York (1968), Chapter 3, which is herein incorporated by reference. Alternatively, the unique arrangement of atoms in spatial relation within the crystalline lattice may be characterized according to the observed fractional atomic coordinates. Another means of characterizing the crystalline structure is by powder X-ray diffraction analysis in which the experimental or observed diffraction profile is compared to a simulated profile representing pure powder material, both run at the same analytical temperature, and measurements for the subject form characterized as a series of 2θ values.

Other means of characterizing the form may be used, such as solid state nuclear magnetic resonance (SSNMR), differential scanning calorimetry (DSC) and thermal gravimetric analysis (TGA). These parameters may also be used in combination to characterize the subject form.

Form A crystals may be characterized by unit cell parameters substantially equal to the following:

Cell Dimensions:
  a=9.86 (5) Å
  b=29.245 (6) Å
  c=8.327 (2) Å
  α=93.56 (2)°
  β=114.77 (3)°
  γ=80.49 (3)°

Space group 1

Molecules/asymmetric unit 2 wherein the crystalline form is at about +22° C.

Form A may be characterized by fractional atomic coordinates substantially as listed in Table 3 and the crystal structure substantially as shown in FIG. 2.

Form A may be characterized by simulated and observed powder X-ray diffraction patterns substantially as shown in FIG. 1.

Form A may be characterized by a differential scanning calorimetry (DSC) thermogram having an endotherm with peak onset at about 165.6° C. substantially as shown in FIG. 3.

Form A may be characterized by a thermal gravimetric analysis (TGA) curve having a negligible weight loss up to about 100° C. to 150° C. substantially as shown in FIG. 4.

Form A may be characterized by the solid-state NMR (SSNMR) chemical shifts substantially as shown in Table 4 and by the spectrum substantially as shown in FIG. 5.

Form A may be characterized by fractional atomic coordinates substantially as listed in Table 5.

Form A salt may be characterized by moisture-sorption isotherms with about 0.1% weight gain in the range from 25 to 75% RH at 25° C.

In one aspect of the present invention, Pattern C may be characterized by the observed powder X-ray diffraction pattern substantially as shown in FIG. 5.

In a different aspect of the present invention, Pattern C may be characterized by a differential scanning calorimetry thermogram substantially as shown in FIG. 7 having an endotherm typically in the range from about 76.7 to about 96.6° C. and from about 156.8 to about 165.9° C.

In a different aspect of the present invention, Pattern C may be characterized by a thermal gravimetric analysis curve having a weight loss of about 2.4% at about 125° C. and a weight loss of about 4.4% up to about 190° C. substantially as shown in FIG. 8.

In accordance with the present invention, Form E3 may be characterized by crystallographic data as shown in Table 5, substantially equal to the following:
  a=10.749 Å
  b=13.450 (4) Å
  c=9.250 (2) Å
  α=98.33 (2)°
  β=95.92 (3)°
  γ=102.82 (3)°

Space group P1

Molecules/asymmetric unit 1 when the crystalline form is at about −23° C.

In a different aspect of the present invention, Form E3 may be characterized by fractional atomic coordinates substantially as listed in Table 6.

In a different aspect of the present invention, Form E3 may be characterized by simulated and observed powder X-ray diffraction patterns substantially as shown in FIG. 9.

In a different aspect of the present invention, Form E3 may be characterized by a differential scanning calorimetry thermogram having an endotherm typically within the range from about 89.4 to about 96.6° C. substantially as shown in FIG. 11.

In a different aspect of the present invention, Form E3 may be characterized by a thermal gravimetric analysis curve having a weight loss of about 14.7% at about 150° C. substantially as shown in Table 8.

In a different aspect of the invention, Form E3 may be characterized by the crystal structure substantially as shown in FIG. 10.

DETAILED DESCRIPTION OF THE INVENTION

Figure 1:
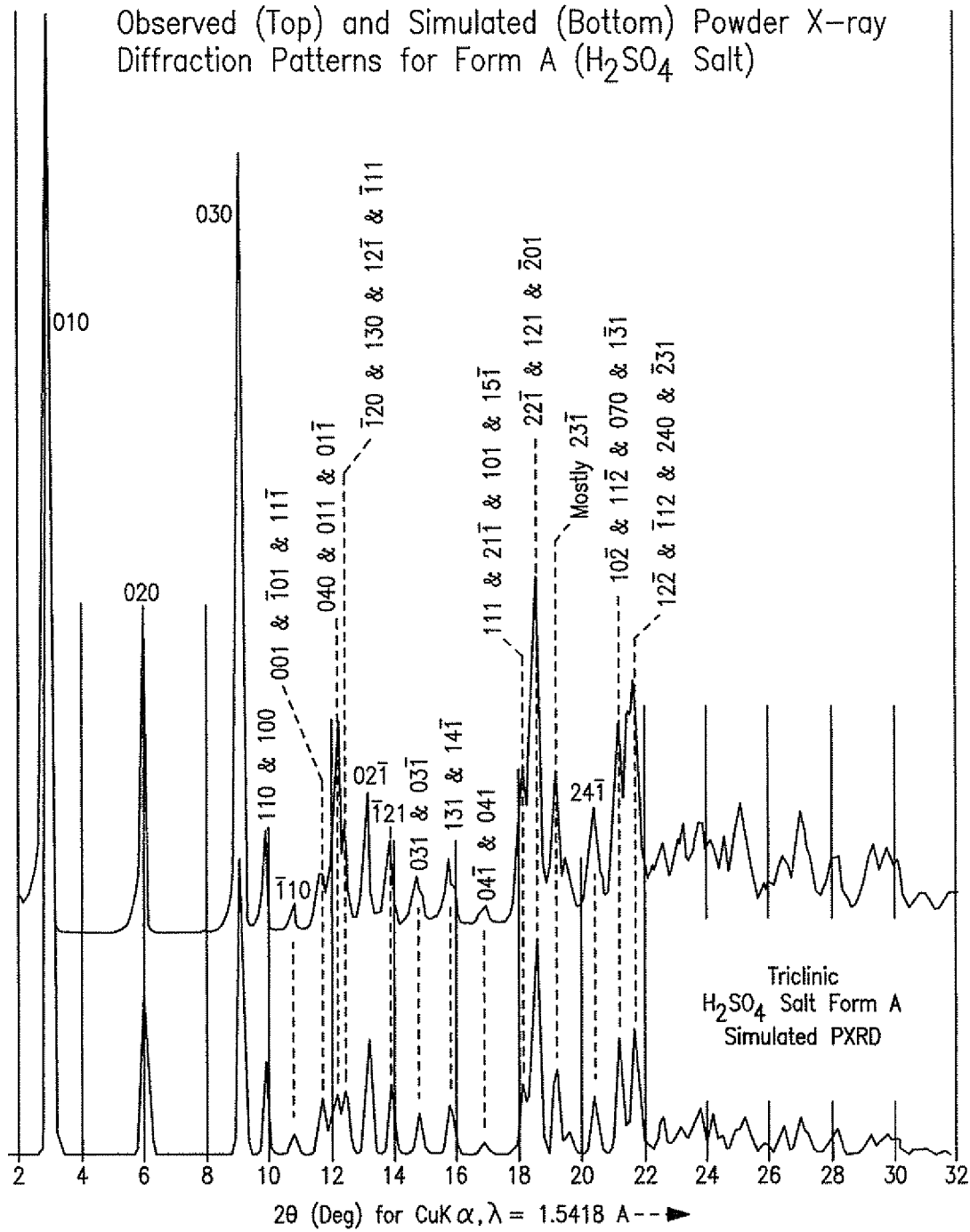
FIG. 1 shows calculated (simulated) (22° C.) and observed (experimental at room temperature) powder X-ray diffraction patterns (CuKα γ=1.5418 Å) of Form A.

The present invention provides, at least in part, forms of atazanavir bisulfate, namely, Form E3 and Pattern C, as novel materials, in particular in pharmaceutically acceptable form. The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In certain preferred embodiments, crystalline forms of free base I and salts thereof are in substantially pure form. The term "substantially pure", as used herein, means a compound having a purity greater than about 90% including, for example, about 91%, about 92%, about 93%, about 94%, about 95%, about 96%, about 97%, about 98%, about 99%, and about 100%.

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further contains molecules of a solvent or solvents incorporated into the crystalline structure. The solvent molecules in the solvate may be present in a regular arrangement and/or a non-ordered arrangement. The solvate may contain either a stoichiometric or nonstoichiometric amount of the solvent molecules. For example, a solvate with a nonstoichiometric amount of solvent molecules may result from partial loss of solvent from the solvate.

Samples of the crystalline forms may be provided with substantially pure phase homogeneity, indicating the presence of a dominant amount of a single crystalline form and optionally minor amounts of one or more other crystalline forms. The presence of more than one crystalline form in a sample may be determined by techniques such as powder X-ray diffraction (PXRD) or solid state nuclear magnetic resonance spectroscopy (SSNMR). For example, the presence of extra peaks in the comparison of an experimentally measured PXRD pattern with a simulated PXRD pattern may indicate more than one crystalline form in the sample. The simulated PXRD may be calculated from single crystal X-ray data. see Smith, D. K., "*A FORTRAN Program for Calculating X-Ray Powder Diffraction Patterns*," Lawrence Radiation Laboratory, Livermore, Calif., UCRL-7196 (April 1963). Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and Jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture.

Crystals of drugs, including polymorphs, methods of preparation, and characterization of drug crystals are discussed in *Solid-State Chemistry of Drugs*, S. R. Byrn, R. R. Pfeiffer, and J. G. Stowell, 2$^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility. Suitable solvents for preparing crystals include polar and nonpolar solvents.

In one method to prepare crystals, atazanavir bisulfate is suspended and/or stirred in a suitable solvent to afford a slurry, which may be heated to promote dissolution. The term "slurry", as used herein, means a saturated solution of atazanavir bisulfate or a salt thereof, which may also contain an additional amount of atazanavir bisulfate or salt thereof to afford a heterogeneous mixture of atazanavir bisulfate or salt thereof and a solvent at a given temperature. Suitable solvents in this regard include, for example, polar aprotic solvents, and polar protic solvents, and mixtures of two or more of these as disclosed herein.

Seed crystals may be added to any crystallization mixture to promote crystallization. As will be clear to the skilled artisan, seeding is used as a means of controlling growth of a particular crystalline form or as a means of controlling the particle size distribution of the crystalline product. Accordingly, calculation of the amount of seeds needed depends on the size of the seed available and the desired size of an average product particle as described, for example, in "Programmed cooling of batch crystallizers," J. W. Mullin and J. Nyvlt, *Chemical Engineering Science* (1971) 26:369-377. In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystal form (i.e. change to amorphous or to another polymorph).

A cooled mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as SSNMR, DSC, PXRD, or the like, to assure formation of the preferred crystalline form of the product. The resulting crystalline form is typically produced in an amount of greater than about 70 weight % isolated yield, but preferably greater than 90 weight % based on the weight of atazanavir bisulfate originally employed in the crystallization procedure. The product may be comilled or passed through a mesh screen to delump the product, if necessary.

Crystalline forms may be prepared directly from the reaction medium of the final process step for preparing atazanavir bisulfate. This may be achieved, for example, by employing in the final process step a solvent or mixture of solvents from which atazanavir bisulfate may be crystallized. Alternatively, crystalline forms may be obtained by distillation or solvent addition techniques. Suitable solvents for this purpose include any of those solvents described herein, including protic polar solvents such as alcohols, and aprotic polar solvents such as ketones.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like. By way of general guidance, the reaction solution may be distilled to about {fraction (1/10)} the original volume before solvent replacement is carried out. The reaction may be sampled and assayed to determine the extent of the reaction and the wt % product in accordance with standard process techniques. If desired, additional reaction solvent may be added or removed to optimize reaction concentration. Preferably, the final concentration is adjusted to about 50 wt % at which point a slurry typically results.

It may be preferable to add solvents directly to the reaction vessel without distilling the reaction mixture. Preferred solvents for this purpose are those which may ultimately participate in the crystalline lattice as discussed above in connection with solvent exchange. Although the final concentration may vary depending on desired purity, recovery and the like, the final concentration of free base I in solution is preferably about 4% to about 7%. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

The various forms described herein may be distinguishable from one another through the use of various analytical techniques known to one of ordinary skill in the art. Such techniques include, but are not limited to, solid state nuclear magnetic resonance (SSNMR) spectroscopy, X-ray powder diffraction (PXRD), differential scanning calorimetry (DSC), and/or thermogravimetric analysis (TGA).

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed and the shape or morphology of the crystal. It should be further understood that relative intensities may also vary depending upon experimental conditions and, accordingly, the exact order of intensity should not be taken into account. Additionally, a measurement error of diffraction angle for a conventional X-ray diffraction pattern is typically about 0.2% or less, preferably about 0.1% (as discussed hereinafter), and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

The term "Form" as used herein with respect to Form A and Form E3 refers to a homogeneous crystal structure.

The term "Pattern" as used herein with respect to Pattern C material refers to a characteristic x-ray diffraction pattern.

The term "atazanavir bisulfate" as employed herein refers to atazanavir bisulfate as well as atazanavir sulfate.

In carrying out the process of the invention for preparing Form A crystals of atazanavir bisulfate salt, a modified cubic crystallization technique is employed wherein atazanavir free base is dissolved in an organic solvent in which the atazanavir bisulfate salt is substantially insoluble and includes acetone, a mixture of acetone and N-methylpyrrolidone, ethanol, a mixture of ethanol and acetone and the like, to provide a solution having a concentration of atazanavir free base within the range from about 6.5 to about 9.7% by weight, preferably from about 6.9 to about 8.1% by weight atazanavir free base.

The solution of atazanavir free base is heated at a temperature within the range from about 35 to about 55° C., preferably from about 40 to about 50° C., and reacted with an amount of concentrated sulfuric acid (containing from about 95 to about 100% $H_2SO_4$) to react with less than about 15%, preferably from about 5 to less than about 12%, more preferably from about 8 to about 10% by weight of the total atazanavir free base. Thus, the starting solution of atazanavir free base will be initially reacted with less than about 15%, preferably from about 5 to about 12%, by weight of the total amount of sulfuric acid to be employed. During the reaction, the reaction mixture is maintained at a temperature within the range from about 35 to about 55° C., preferably from about 40 to about 50° C.

The reaction is allowed to continue for a period from about 12 to about 60 minutes, preferably from about 15 to about 30 minutes.

The reaction mixture is seeded with crystals of Form A atazanavir bisulfate employing an amount of seeds within the range from about 0.1 to about 80% by weight, preferably from about 3 to about 8% by weight, based on the weight of atazanavir free base remaining in the reaction mixture while maintaining the reaction mixture at a temperature within the range from about 35 to about 55° C., preferably from about 40 to about 50° C.

The reaction is allowed to continue until crystallization begins. Thereafter, sulfuric acid is added in multiple stages at an increasing rate according to the cubic equation as described below to form atazanavir bisulfate which upon drying produces Form A crystals.

The crystal particle size and morphology of the atazanavir bisulfate salt formed are dependent on the addition rate of the sulfuric acid, which determines the crystallization rate. It has been found that a modified "cubic" crystallization technique (acid added at an increasing rate according to a cubic equation) provides relatively larger, more well defined atazanavir bisulfate crystals, along with a narrower particle size range and fewer fines, than a constant addition rate crystallization. The slow initial acid flow rate has been shown to favor crystal growth over secondary nucleation. Thus, as the surface area increases with particle size, the seed bed is able to accept the increasing acid flow rate without inducing secondary nucleation. The slow initial addition rate allows time for the crystals to grow larger, increasing the mean size. The cubic crystallization provides a less compressible filter cake, which aids in effective cake deliquoring and washing, as well as giving a more easily dried product with fewer hard lumps than the constant addition rate crystallized product.

The cubic crystallization method employed is a temperature controlled crystallization derived from Mullin, "Crystallization, $3^{rd}$ Ed.", 1993, Butterworth-Heineman, Pubs. and is defined by the following simplified equation:

$$T = T_{max} - (T_{max} - T_{min}) \times \left(\frac{time}{time_{total}}\right)^3 \quad (1)$$

where $T_{max}$=Starting temperature for crystallization
$T_{min}$=Ending temperature for crystallization
time=Elapsed time in crystallization
$time_{total}$=Total crystallization time.

Since the crystallization of atazanavir bisulfate is controlled by the addition rate of sulfuric acid, the temperature variable is replaced with acid volume in Equation (1). In this equation, the variable representing the minimum volume is removed.

$$V_{time} = V_{total} \times \left(\frac{time}{time_{total}}\right)^3 \quad (2)$$

where $V_{time}$=Volume of sulfuric acid added during elapsed time period
$V_{total}$=Total volume of acid representing the 90% charge
time=Elapsed time in crystallization
$time_{total}$=Total crystallization time.

Equation (2) is referred to as "the cubic equation."

By controlling the crystallization rate using this expression, nucleation is controlled within acceptable limits as the system maintains a constant low level of supersaturation.

Figure 2:
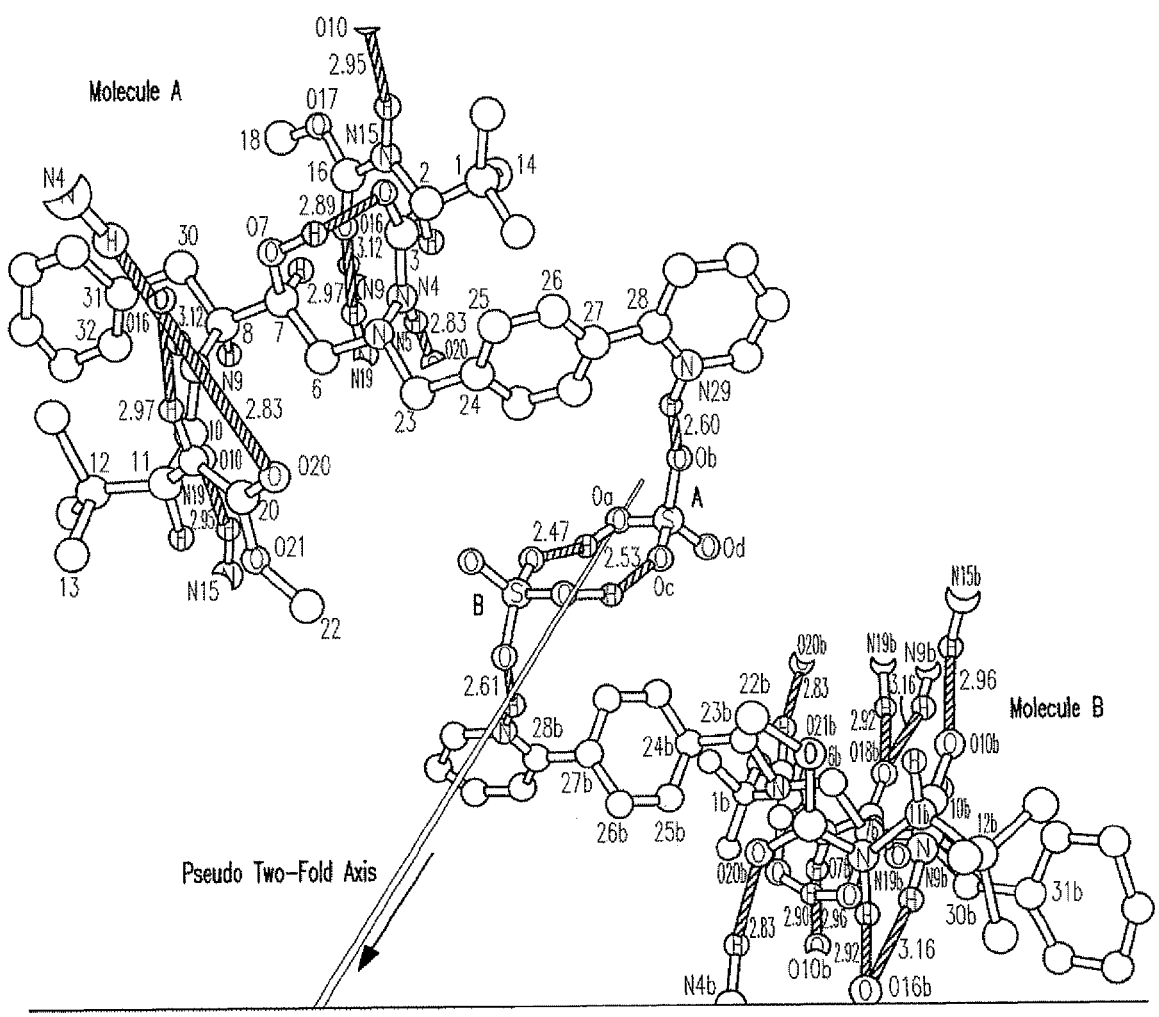
FIG. 2 shows the crystal structure of Form A.

Form A crystals are identified by powder x-ray diffraction pattern and crystal structure as shown in FIGS. 1 and 2, respectively.

The Form A crystals of atazanavir bisulfate or the Pattern C material as well as Form E3 prepared as described above are the final atazanavir bisulfate and can be employed as drug products for administration to patients.

In accordance with the process of the invention, Pattern C material may be prepared by exposing Form A crystals to water followed by drying.

In another process in accordance with the present invention, Pattern C material may be formed by exposing crystals of Form A to high relative humidity of greater than about 95% RH, preferably from about 95 to about 100% RH (water vapor), for at least 24 hours, preferably from about 24 to about 48 hours.

In another embodiment of the invention, Pattern C material is prepared by wet granulating atazanavir bisulfate Form A to produce granules of atazanavir bisulfate and then drying the granules.

In carrying out the wet granulation process, the atazanavir bisulfate will be granulated in water and dried at a temperature within the range from about 40 to about 80° C., preferably within the range from about 50 to about 60° C. The drying step will be preferably carried out for at least about 2 hours, up to about 20 hours, preferably from about 8 to about 10 hours.

The Pattern C material may also be formed by wet granulating atazanavir bisulfate Form A in the presence of conventional pharmaceutical excipients, for example, one or more bulking agents, preferably lactose, one or more disintegrants, preferably crospovidone, and drying as described above to form Pattern C material in admixture with the excipients.

It is the Pattern C material, Form A or Form E3, preferably Pattern C material, which is formulated for administration in the treatment of diseases caused by viruses as described hereinafter.

Figure 3:
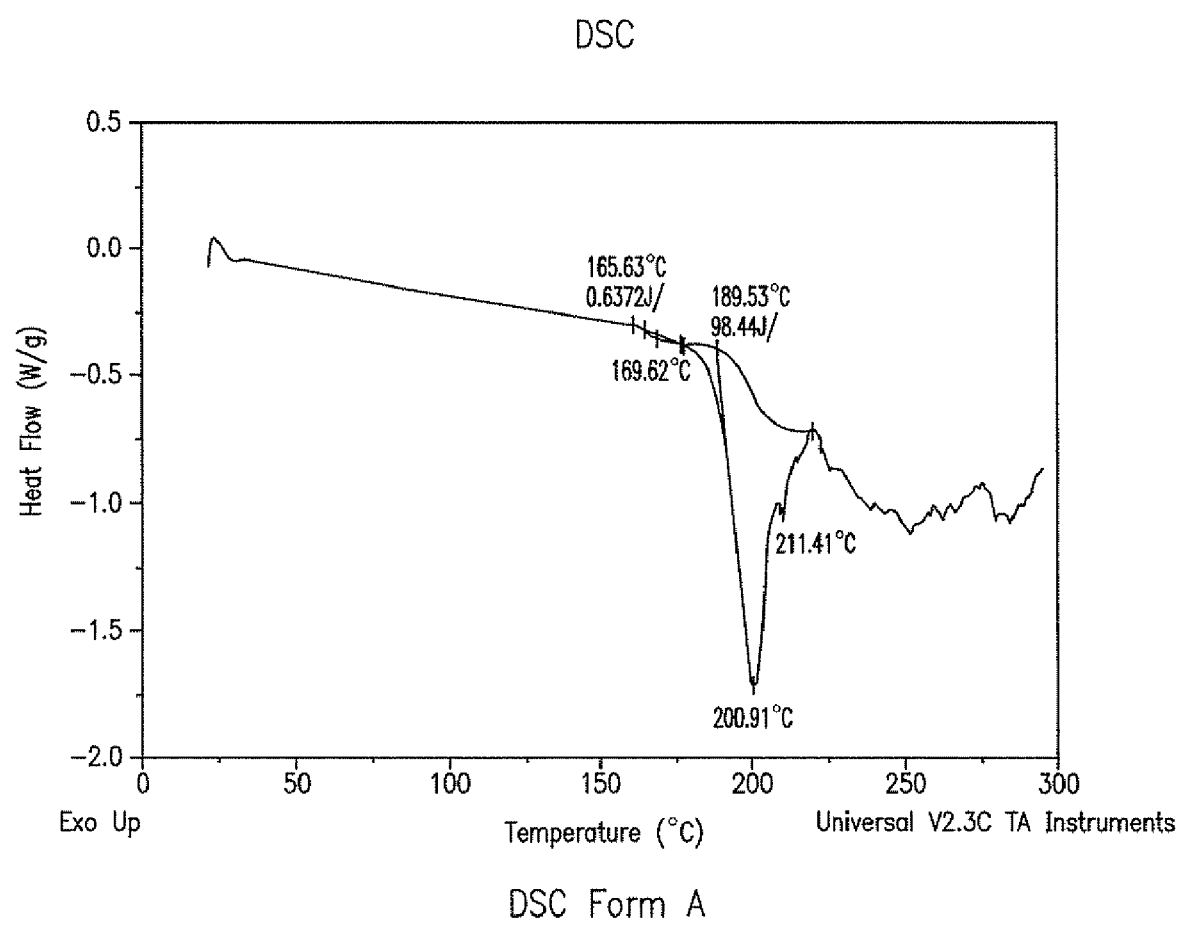
FIG. 3 shows a differential scanning calorimetry (DSC) thermogram of Form A.
Figure 4:
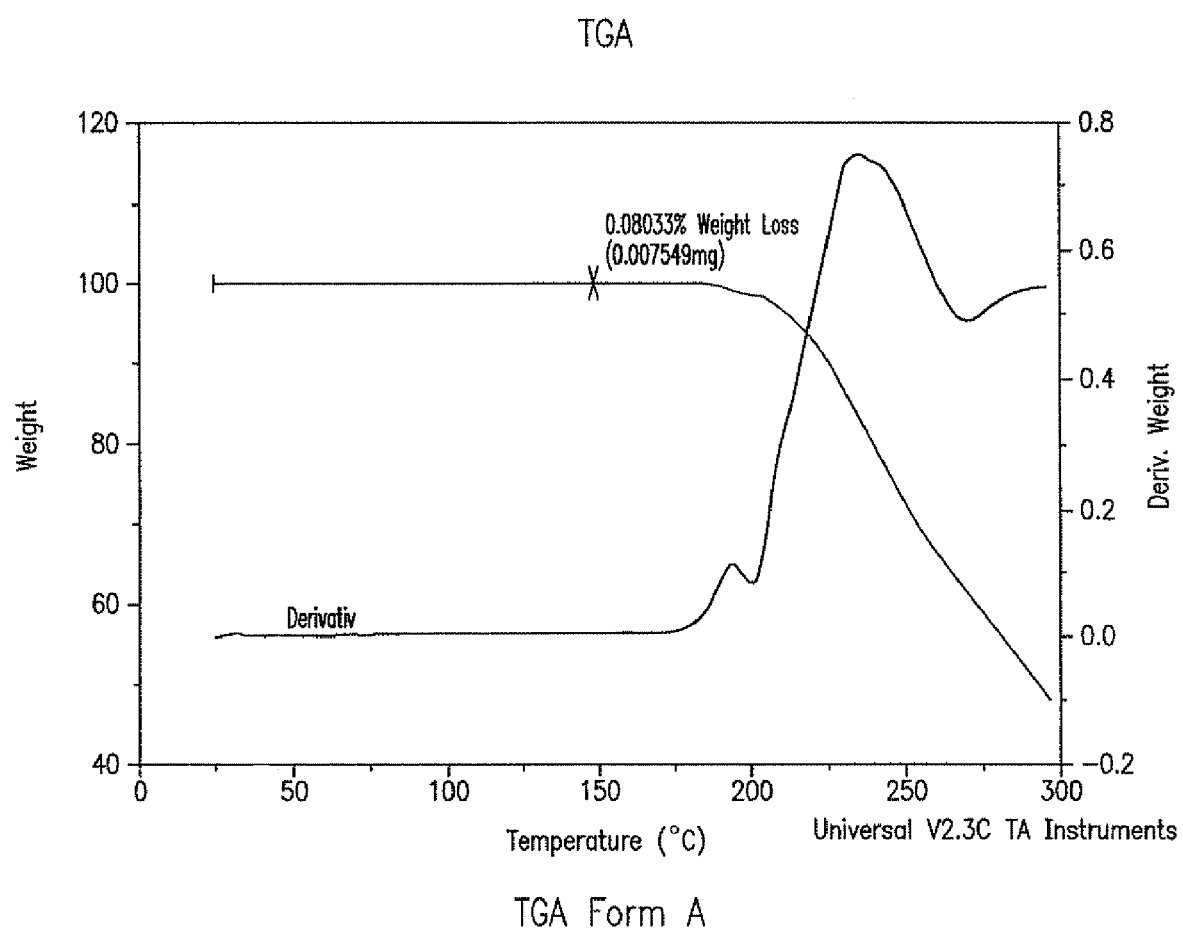
FIG. 4 shows a thermal gravimetric analysis curve (TGA) of Form A.
Figure 5:
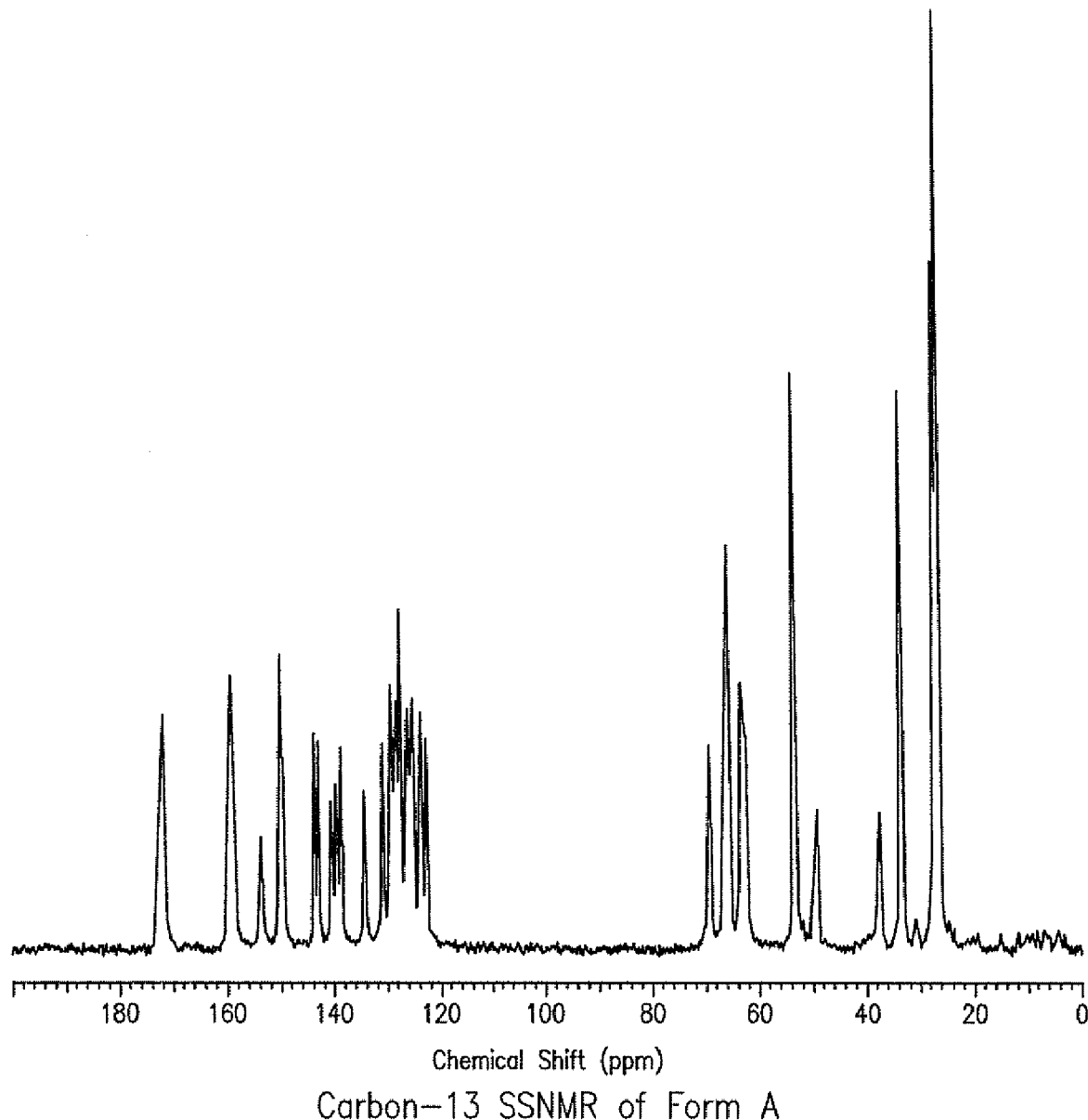
FIG. 5 shows a C-13 solid state NMR of Form A.

Pattern C material is characterized by its powder x-ray diffraction pattern as shown in FIG. 3.

The Form E3 is prepared by slurrying atazanavir free base in ethanol, treating the slurry with concentrated sulfuric acid employing a molar ratio of acid:free base with the range from about 1:1 to about 1.1:1, heating the resulting solution at from about 30 to about 40° C., seeding the solution with ethanol wet E3 crystals of atazanavir sulfate, treating the mixture with heptane (or other solvent such as hexane or toluene), filtering, and drying to yield atazanavir bisulfate Form E3 (triethanol solvate).

The seeding step will employ an amount of seeds to effect formation of E3 crystals, for example a molar ratio of atazanavir bisulfate E-3 seeds:free base within the range from about 0.02:1 to about 0.04:1.

Figure 6:
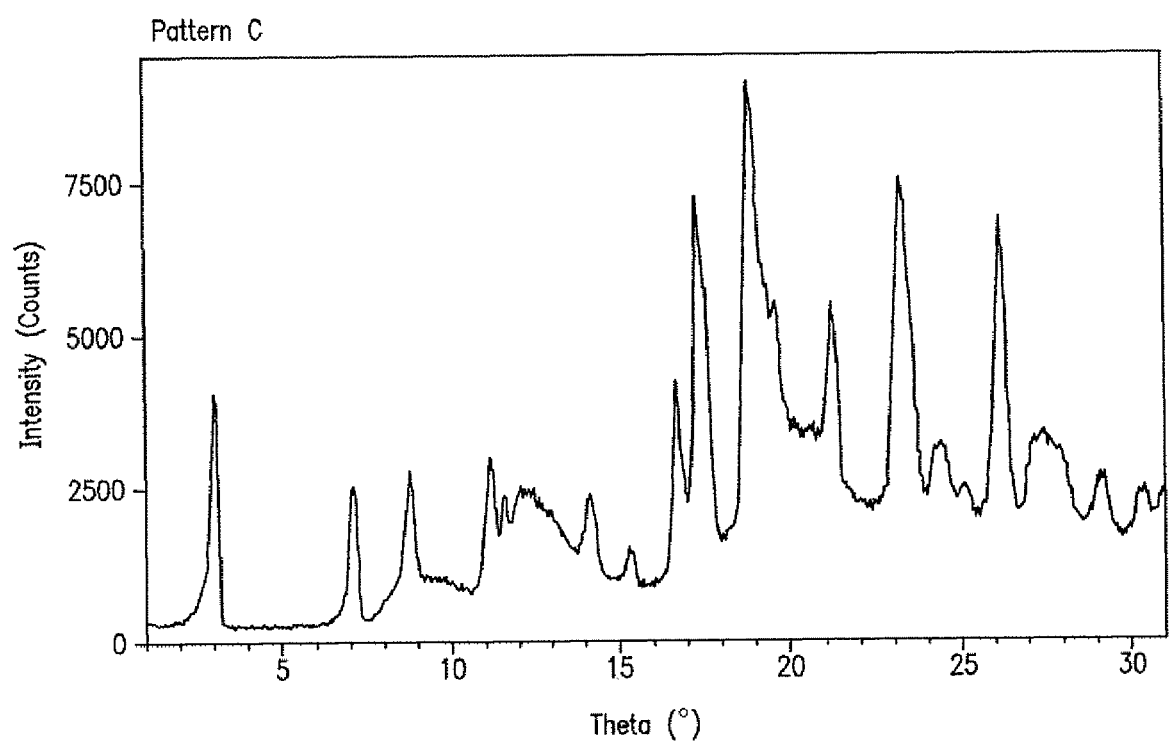
FIG. 6 shows an observed (experimental at room temperature) powder X-ray diffraction pattern (CuKα γ=1.5418 Å) of Pattern C.
Figure 7:
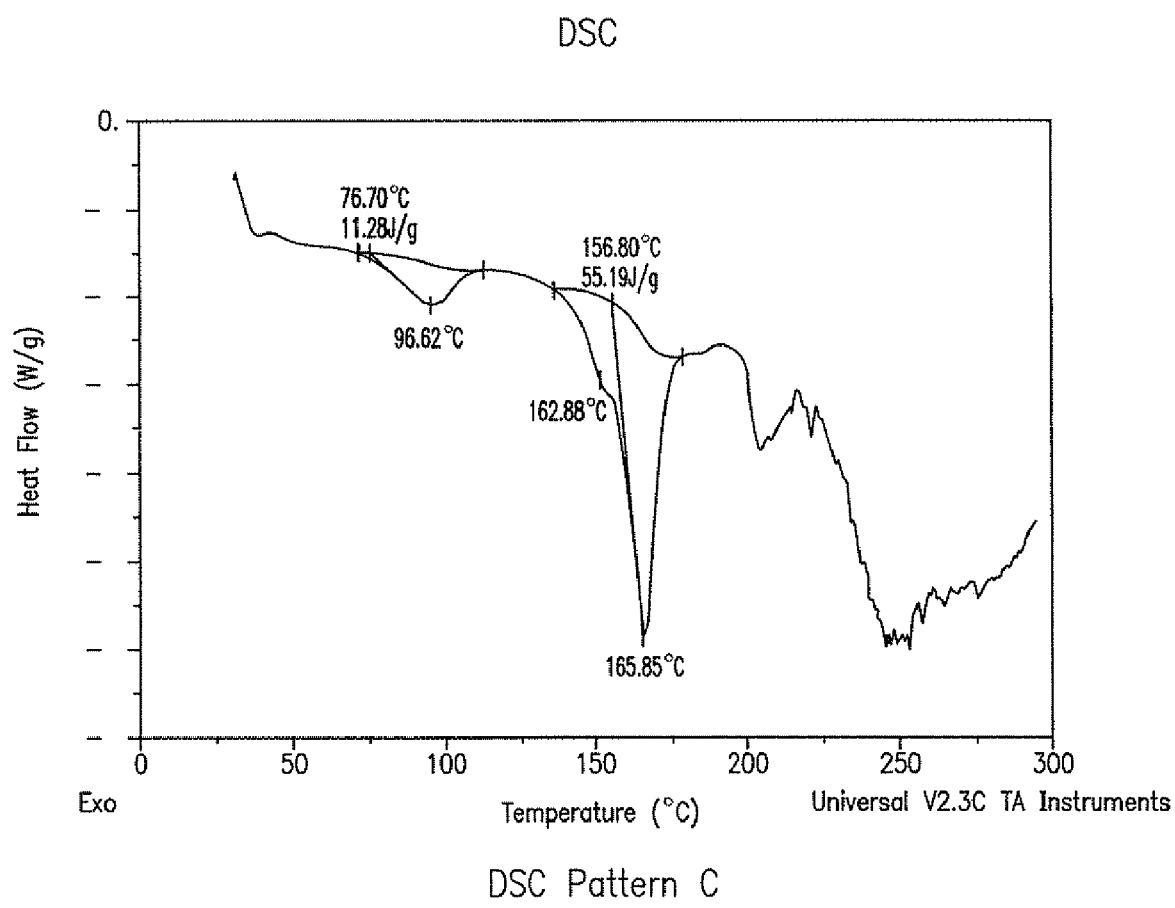
FIG. 7 shows a differential scanning calorimetry thermogram of Pattern C.

Form E3 is identified by powder x-ray diffraction pattern as shown in FIG. 7 and crystal structure as shown in FIG. 6.

In accordance with the present invention, the atazanavir in the form of its free base is prepared by treating a solution of a protected triamine salt of the structure

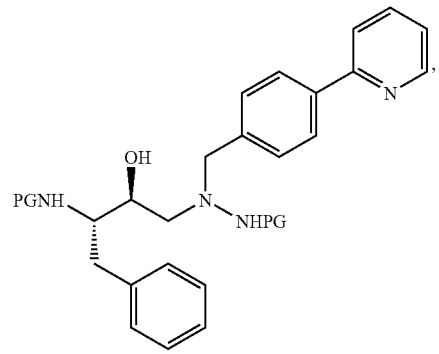

(where PG represents a protecting group such as t-butyloxycarbonyl (Boc) or trifluoroacetyl, preferably Boc, with an acid, preferably hydrochloric acid (where Boc is used), or a base (where trifluoroacetyl is used) in the presence of an organic solvent such as methylene chloride, tetrahydrofuran, or methanol, which solvent is preferably methylene chloride, at a temperature within the range from about 25 to about 50° C., preferably from about 30 to about 40° C., to form the triamine acid salt, preferably the hydrogen chloride salt of the structure

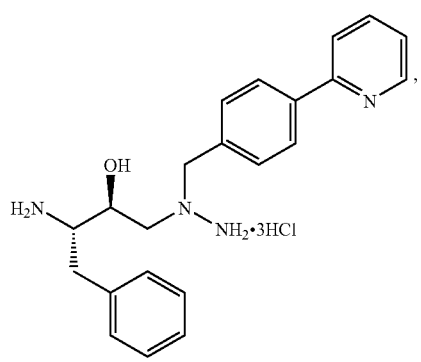

and without isolating the triamine acid salt, reacting the triamine acid salt with an active ester of an acid of the structure

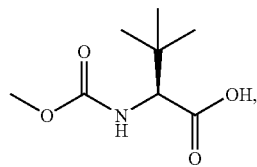

preferably the active ester of the structure

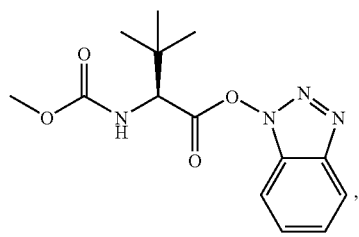

in the presence of a base such as $K_2HPO_4$, diisopropylethylamine, N-methylmorpholine, sodium carbonate, or potassium carbonate, preferably $K_2HPO_4$, in the presence of an organic solvent such as methylene chloride, a mixture of ethyl acetate and butyl acetate, acetonitrile or ethyl acetate, preferably methylene chloride, at a temperature within the range from about 25 to about 50° C., preferably from about 30 to about 40° C. to form atazanavir free base.

The protected triamine starting material is prepared by reacting the epoxide

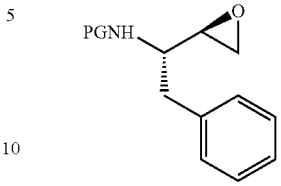

where PG is preferably Boc such as N-(tert-butyloxycarbonyl)-2(S)-amino-1-phenyl-3(R)-3,4-epoxy-butane, with the hydrazine carbamate

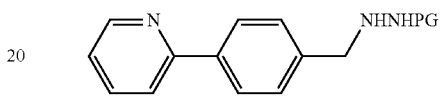

where PG is preferably Boc in the presence of isopropyl alcohol or other alcohol such as ethanol or butanol.

Atazanavir bisulfate is useful for administration to a warm-blooded animal, especially a human being, for the treatment or prevention of a disease that is responsive to inhibition of a retroviral protease, especially a retroviral aspartate protease, such as HIV-I or HIV-II gag protease, for example a retroviral disease, such as AIDS or its preliminary stages.

Atazanavir bisulfate, especially Pattern C material, Form A or Form E3, preferably Pattern C material or Form A, may be used in a method of treating diseases caused by viruses, especially by retroviruses, especially AIDS or its preliminary stages, wherein a therapeutically effective amount of atazanavir bisulfate Pattern C material, Form A or Form E3 is administered in a dose that is effective in the treatment of said disease especially to a warm-blooded animal, for example a human being, who on account of one of the mentioned diseases, especially AIDS or its preliminary stages, requires such treatment. The preferred dose to be administered to warm-blooded animals, for example human beings of approximately 70 kg body weight, is from about 3 mg to about 1.5 g, preferably from about 10 mg to about 1.25 g, for example from about 50 mg to about 600 mg per person per day, divided preferably into 1 to 4 single doses which may, for example, be of the same size. Usually, children receive half of the adult dose. It is preferably administered orally.

Atazanavir bisulfate Pattern C material, Form A or Form E3 is employed for the above described pharmaceutical uses. Suitable compositions containing Pattern C material or Form A or Form E3 for oral administration include tablets, powders, capsules, and elixirs. About 10 to 600 mg of active ingredient is compounded with physiologically acceptable vehicle, carrier, excipient, binder, preservative, stabilizer, flavoring, etc., in a unit dose form as called for by accepted pharmaceutical practice.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores, capsules or powders for oral use. It is also possible for the active ingredients to be incorporated into plastic carriers that allow the active ingredients to diffuse or be released in measured amounts.

The bulking agents or fillers will be present in the pharmaceutical compositions of the invention in an amount within the range from about 0 to about 95% by weight and preferably from about 10 to about 85% by weight of the composition. Examples of bulking agents or fillers suitable for use herein include, but are not limited to, cellulose derivatives such as microcrystalline cellulose or wood cellulose, lactose, sucrose, starch, pregelatinized starch, dextrose, mannitol, fructose, xylitol, sorbitol, corn starch, modified corn starch, inorganic salts such as calcium carbonate, calcium phosphate, dicalcium phosphate, calcium sulfate, dextrin/dextrates, maltodextrin, compressible sugars, and other known bulking agents or fillers, and/or mixtures of two or more thereof, preferably lactose.

A binder will be optionally present in the pharmaceutical compositions of the invention in an amount within the range from about 0 to about 20% weight, preferably from about 1 to about 10% by weight of the composition. Examples of binders suitable for use herein include, but are not limited to, hydroxypropyl cellulose, corn starch, pregelatinized starch, modified corn starch, polyvinyl pyrrolidone (PVP) (molecular weight ranging from about 5,000 to about 80,000, preferably about 40,000), hydroxypropylmethyl cellulose (HPMC), lactose, gum acacia, ethyl cellulose, cellulose acetate, as well as a wax binder such as carnauba wax, paraffin, spermaceti, polyethylenes or microcrystalline wax, as well as other conventional binding agent and/or mixtures by two or more thereof, preferably hydroxypropyl cellulose.

The disintegrant will be optionally present in the pharmaceutical composition of the invention in an amount within the range from about 0 to about 20% by weight, preferably from about 0.25 to about 15% by weight of the composition. Examples of disintegrants suitable for use herein include, but are not limited to, croscarmellose sodium, crospovidone, potato starch, pregelatinized starch, corn starch, sodium starch glycolate, microcrystalline cellulose, or other known disintegrant, preferably croscarmellose sodium.

The lubricant will be optionally present in the pharmaceutical composition of the invention in an amount within the range from about 0.1 to about 4% by weight, preferably from about 0.2 to about 2% by weight of the composition. Examples of tableting lubricants suitable for use herein include, but are not limited to, magnesium stearate, zinc stearate, calcium stearate, talc, carnauba wax, stearic acid, palmitic acid, sodium stearyl fumarate or hydrogenated vegetable oils and fats, or other known tableting lubricants, and/or mixtures of two or more thereof, preferably magnesium stearate.

Capsules are hard gelatin capsules and also soft, sealed capsules made of gelatin and a plasticizer, such as glycerol or sorbitol. The hard gelatin capsules may include the active ingredient in the form of granules, for example with fillers, such as lactose, binders, such as starches, crospovidone and/or glidants, such as talc or magnesium stearate, and if desired with stabilizers. In soft gelatin capsules the active ingredient is preferably dissolved or suspended in suitable oily excipients, such as fatty oils, paraffin oil or liquid polyethylene glycols, it likewise being possible for stabilizers and/or antibacterial agents to be added.

The following examples represent preferred embodiments of the invention.

Example 1

1-[4-(Pyridin-2-yl)phenyl]-5(S)-2,5-bis{[N-(methoxycarbonyl)-L-tert-leucinyl]amino}-4-(S)-hydroxy-6-phenyl-2-azahexane, Bisulfate salt (Form A) (Atazanavir bisulfate—Form A)

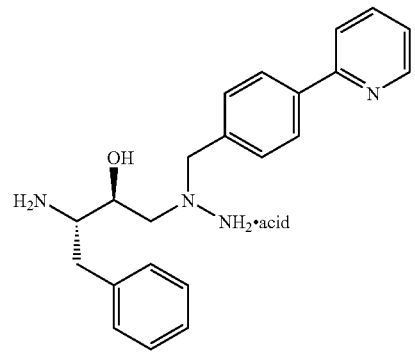

A. (1-[4-(Pyridin-2-yl)phenyl]-5(S)-2,5-bis[tert-butyloxycarbonyl)amino]-4(S)-hydroxy-6-phenyl-2-azahexane.3HCl (Triamine.3HCl Salt))

To a 1000 mL, 3-neck, round-bottom flask fitted with mechanical stirrer, nitrogen inlet and temperature probe was added the protected triamine 1-[4-(pyridin-2-yl)phenyl]-5(S)-2,5-bis[tert-butyloxycarbonyl)amino]-4(S)-hydroxy-6-phenyl-2-azahexane

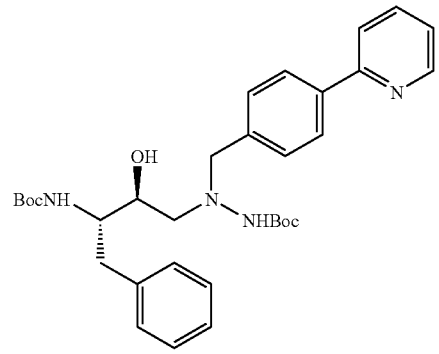

(100 g, 0.178 mol), and $CH_2Cl_2$ (500 mL; 5 mL/g of protected triamine input) (prepared as described in Z. Xu et al., Process Research and Development for an Efficient Synthesis of the HIV Protease Inhibitor BMS-232,632, Organic Process Research and Development, 6, 323-328 (2002)) and the resulting slurry was agitated while maintaining the temperature at from about 5 to about 22° C.

Concentrated hydrochloric acid (68 mL, 0.82 mole, 4.6 eq.) was added to the reaction mixture at a rate such that the temperature of the reaction mixture remained between 5 and 30° C. The reaction mixture was heated to 30 to 40° C. and agitated until the reaction was judged complete by HPLC assay.

Water was added (70-210 mL, 0.7-2.1 mL/g protected triamine input) to the reaction mixture, the reaction mixture was agitated for 15 minutes and the phases were allowed to separate. The upper, product (triamine.3HCl salt)-rich aqueous oil was transferred to an addition funnel.

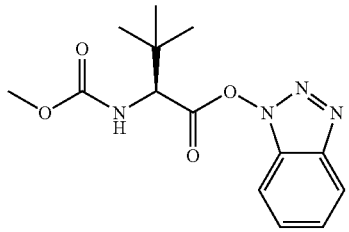

B. Active Ester of N-methoxycarbonyl-L-tert-leucine

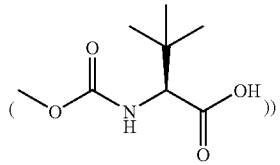

To a 3000 mL, 3-neck round bottom flask fitted with mechanical stirrer, addition funnel, nitrogen inlet, and temperature probe was added N-methoxycarbonyl-L-tert-leucine (77.2 g, 0.408 mol, 2.30 eq.), 1-hydroxybenzotriazole (HOBT) (60.8 g, 0.450 mol, 2.53 eq.), and N-ethyl N'-dimethylaminopropyl carbodiimide (EDAC) (82.0 g, 0.430 mol 2.42 eq.), followed by $CH_2Cl_2$ (880 mL; 8.8 mL/g of protected triamine input) and the mixture was stirred at ambient temperature (18-25° C.) until formation of the active ester is complete, as judged by HPLC.

C. 1-[4-(Pyridin-2-yl)phenyl]-5(S)-2,5-bis{[N-(methoxycarbonyl)-L-tert-leucinyl]amino}-4(S)-hydroxy-6-phenyl-2-azahexane (atazanavir free base)

Anhydrous dibasic potassium phosphate ($K_2HPO_4$; 226 g., 1.30 mol, 7.30 eq. wrt protected triamine) was dissolved in 1130 mL of water (11.3 mL/g of protected amine; 5 mL/g of $K_2HPO_4$).

The $K_2HPO_4$ solution was added to the active ester solution prepared in Part B. To the stirred active ester/aqueous $K_2HPO_4$ mixture was slowly added the aqueous solution of Part A hydrogen chloride salt over a period of 1.5 to 2.0 h while maintaining agitation and a pot temperature between 5 and 20° C.

After the addition of the solution of the Part A hydrogen chloride salt was complete, the reaction mixture (coupling reaction) was heated to 30-40° C. and agitated until the coupling reaction was judged complete by HPLC assay.

The coupling mixture was cooled to 15 to 20° C. and the lower, product rich organic phase was separated from the upper, spent aqueous phase.

The product rich organic phase was washed with 1M $NaH_2PO_4$ (880 mL; pH=1.5; 8.8 mL/g of protected triamine input; 5 mole eq. wrt protected triamine), the phases were allowed to separate, and the spent aqueous phase was removed.

The washed product rich organic phase was stirred with 0.5 N NaOH (800 mL; 8 mL/g of protected triamine input) until HPLC assay of the rich organic phase showed the active esters to be below 0.3 I.I. each. The phases were allowed to separate and the spent aqueous phase was removed.

The rich organic phase was washed with 5% $NaH_2PO_4$ (450 mL, 4.5 mL/g of protected triamine input; pH=4.3), the phases were allowed to separate and the spent aqueous phase was removed.

The rich organic phase was washed with 10 w/v % NaCl (475 mL, 4.75 mL/g of protected triamine input) and the spent aqueous phase was removed.

The concentration of title free base in solution was 120 to 150 mg/mL with an in-process calculated yield of 95-100 mol %.

D. Solvent Exchange from $CH_2Cl_2$ into Acetone/N-Methylpyrrolidone

To the rich Part C free base solution in a 3000 mL, 3-neck round-bottom flask fitted with mechanical stirrer, temperature probe, and distillation condenser, was added N-methylpyrrolidone (148 mL; 1.25 mL/g of Part C free base based on in-process quantification assay). The solution was concentrated to ca. 360 mL (2.5-3.5 mL/g of Part C free base) using a jacket temperature of 70° C. or less; 500 mL of acetone (4-5 mL/g of Part C free base) was added to the concentrated solution and the mixture was distilled to a volume of about 400 mL or less.

The acetone addition and distillation were repeated until in-process assay indicated the $CH_2Cl_2$ level had reached the target endpoint. At crystallization volume, the $CH_2Cl_2$ content in the rich organic solution was 0.77 v/v %. Acetone was added to the concentrated free base solution to reach a total solution of 16 mL/g of free base. The bath temperature was maintained at 40-50° C. to prevent crystallization of free base. The solution was polish filtered through a 10-micron or finer filter while maintaining the temperature at 40 to 50° C. The polish filter was rinsed with acetone (125 mL, 1.0 mL/g of free base) and the rinse was added to the rich free base acetone/N-methylpyrrolidone solution which was used in the next step.

E. 1-[4-(Pyridin-2-yl)phenyl]-5(S)-2,5-bis{[N-(methoxycarbonyl)-L-tert-leucinyl]amino}-4(S)-hydroxy-6-phenyl-2-azahexane bisulfate salt About 10% (2 g) of the total charge of concentrated sulfuric acid (19 g, 1.10 eq.) was added to the free base acetone/N-methylpyrrolidone solution of Part D, while maintaining the temperature at 40-50° C., via subsurface addition.

The reaction mixture was seeded with 5.0 wt % (wrt calculated free base in solution) of bisulfate salt. The seeded mixture was agitated at 40-50° C. for at least 30 minutes during which time the bisulfate salt began crystallizing as evidenced by the mixture increasing in opacity during this time.

The remaining sulfuric acid (17.8 g) was added over ca. 5 h in five stages according to the following protocol, defined by a cubic equation, while keeping the temperature at 40-50° C.

The rate of each addition stage was determined according to the cubic equation described hereinbefore and is shown in the table below.

TABLE 1

| Stage | mL/kg/h | mL($H_2SO_4$)/h | g($H_2SO_4$)/h | Duration (min) |
|---|---|---|---|---|
| 1 | 4.62 | 0.579 | 1.065 | 60 |
| 2 | 6.93 | 0.868 | 1.597 | 60 |
| 3 | 16.55 | 2.073 | 3.814 | 60 |
| 4 | 30.26 | 3.790 | 6.974 | 60 |
| 5 | 48.47 | 6.071 | 11.171 | 23 |

After addition of $H_2SO_4$ was complete, the slurry was cooled to 20-25° C. for at least 1 h with agitation. The slurry was agitated at 20-25° C. for at least 1 h. The bisulfate salt was filtered and the mother liquor was recycled as needed to effect complete transfer. The filter cake was washed with acetone (5-10 mL/g of free base; 1200 mL acetone). The bisulfate salt was dried at NMT 55° C. under vacuum until the LOD<1% to produce a crystalline material.

The crystalline product was analyzed by PXRD, DSC and TGA patterns and SSNMR spectrum and found to be (non-solvated) Form A crystals of the title bisulfate (see FIGS. 1 to 5).

TABLE 2

Table of Crystallographic Data
Form A

| T ° C. | a(Å) | b(Å) | c(Å) | α° | β° | γ° | V(Å³) | Z' | sg | dcalc | R |
|---|---|---|---|---|---|---|---|---|---|---|---|
| +22 | 9.861(5) | 29.245(6) | 8.327(2) | 93.56(2) | 114.77(3) | 80.49(3) | 2150(2) | 2 | P1 | 1.240 | 0.06 |

T = temp(° C.) for the crystallographic data.
Z' = number of drug molecules per asymmetric unit

TABLE 3

Table Of Fractional Parameters and Their
Estimated Standard Deviations for Form A

| Atom | x | y | z | B(A2) |
|---|---|---|---|---|
| S1 | 0.3230(4) | 0.5467(1) | 0.5608(5) | 8.0(1) |
| O100 | 0.431(1) | 0.5060(3) | 0.649(1) | 11.1(3) |
| O102 | 0.335(1) | 0.5498(4) | 0.383(1) | 12.0(4) |
| O103 | 0.360(1) | 0.5877(4) | 0.655(2) | 12.0(4) |
| O104 | 0.176(1) | 0.5384(4) | 0.528(1) | 11.8(4) |
| S51 | 0.6177(4) | 0.4505(1) | 0.4003(5) | 7.2(1) |
| O150 | 0.596(1) | 0.4430(4) | 0.564(1) | 12.5(4) |
| O152 | 0.518(1) | 0.4921(4) | 0.317(1) | 13.8(4) |
| O153 | 0.588(1) | 0.4121(3) | 0.289(2) | 12.2(4) |
| O154 | 0.768(1) | 0.4587(4) | 0.454(1) | 12.1(4) |
| O4 | 0.6985(7) | 0.1753(3) | 0.6456(9) | 5.7(2) |
| O7 | 0.1687(8) | 0.1941(3) | 0.3411(9) | 6.5(2) |
| O11 | −0.0352(7) | 0.2482(3) | 0.0308(8) | 5.7(2) |
| O14 | 0.2280(7) | 0.1769(3) | −0.233(1) | 6.1(2) |
| O15 | 0.0399(8) | 0.1335(3) | −0.330(1) | 6.4(2) |
| O17 | 0.6169(7) | 0.2821(3) | 0.963(1) | 7.1(2) |
| O18 | 0.3750(7) | 0.2905(3) | 0.9136(9) | 6.2(2) |
| N2 | 0.5015(9) | 0.2182(3) | 0.902(1) | 4.5(2) |
| N5 | 0.4642(8) | 0.1647(3) | 0.6001(9) | 4.2(2) |
| N9 | 0.2317(9) | 0.2788(3) | 0.256(1) | 5.1(2) |
| N10 | 0.1820(9) | 0.2760(3) | 0.069(1) | 4.6(2) |
| N13 | −0.0148(8) | 0.2083(3) | −0.280(1) | 4.6(2) |
| N39 | −0.087(1) | 0.5265(3) | 0.272(1) | 6.1(2) |
| C1 | 0.491(1) | 0.2627(4) | 0.924(1) | 5.5(3) |
| C3 | 0.6381(9) | 0.1908(3) | 0.892(1) | 4.0(2) |
| C4 | 0.600(1) | 0.1764(4) | 0.702(1) | 4.6(3) |
| C6 | 0.420(1) | 0.1551(4) | 0.403(1) | 5.1(3) |
| C7 | 0.295(1) | 0.1936(4) | 0.297(1) | 5.1(3) |
| C8 | 0.357(1) | 0.2400(4) | 0.346(2) | 5.4(3) |
| C11 | 0.051(1) | 0.2592(4) | −0.028(1) | 4.9(3) |
| C12 | 0.024(1) | 0.2531(4) | −0.223(1) | 4.5(3) |
| C14 | 0.094(1) | 0.1732(4) | −0.280(1) | 4.7(3) |
| C16 | 0.146(2) | 0.0943(5) | −0.342(2) | 10.9(5) |
| C19 | 0.616(1) | 0.3313(4) | 0.996(2) | 8.1(4) |
| C20 | 0.701(1) | 0.1485(4) | 1.025(1) | 5.8(3) |
| C21 | 0.842(1) | 0.1219(5) | 1.007(2) | 7.9(4) |
| C22 | 0.583(2) | 0.1160(5) | 0.997(2) | 8.0(4) |
| C23 | 0.748(2) | 0.1713(5) | 1.215(1) | 8.2(4) |
| C24 | 0.365(1) | 0.1079(4) | 0.356(2) | 6.6(4) |
| C25 | 0.484(1) | 0.0691(4) | 0.470(1) | 6.5(3) |
| C26 | 0.643(2) | 0.0684(5) | 0.520(2) | 8.4(5) |
| C27 | 0.753(2) | 0.0293(6) | 0.622(2) | 11.4(6) |
| C28 | 0.709(3) | −0.0044(7) | 0.691(3) | 15.0(9) |
| C29 | 0.553(2) | −0.0032(5) | 0.644(2) | 14.2(7) |
| C30 | 0.441(2) | 0.0343(5) | 0.534(2) | 10.8(4) |
| C31 | 0.291(1) | 0.3229(4) | 0.311(2) | 5.7(3) |
| C32 | 0.177(1) | 0.3650(4) | 0.259(1) | 5.4(3) |
| C33 | 0.224(1) | 0.4064(4) | 0.262(2) | 6.3(3) |
| C34 | 0.122(1) | 0.4487(5) | 0.233(2) | 6.9(4) |
| C35 | −0.031(1) | 0.4469(4) | 0.189(1) | 4.8(3) |
| C36 | −0.081(1) | 0.4043(4) | 0.180(1) | 5.6(3) |
| C37 | 0.019(1) | 0.3629(4) | 0.218(1) | 5.4(3) |
| C38 | −0.136(1) | 0.4918(4) | 0.170(1) | 5.3(3) |
| C40 | −0.170(1) | 0.5683(4) | 0.279(2) | 7.8(4) |
| C41 | −0.318(2) | 0.5736(5) | 0.158(2) | 9.1(5) |
| C42 | −0.376(1) | 0.5403(4) | 0.035(2) | 9.0(5) |
| C43 | −0.283(1) | 0.4964(5) | 0.039(2) | 8.1(4) |
| C44 | −0.096(1) | 0.2937(4) | −0.345(1) | 6.2(3) |
| C45 | −0.258(1) | 0.2901(5) | −0.366(2) | 8.5(4) |
| C46 | −0.085(2) | 0.2890(6) | −0.530(2) | 10.8(5) |
| C47 | −0.057(2) | 0.3393(5) | −0.265(2) | 8.9(5) |
| O54 | 0.2347(7) | 0.8167(3) | 0.8392(8) | 5.3(2) |
| O57 | 0.7713(8) | 0.7950(3) | 1.0561(9) | 5.9(2) |
| O61 | 0.9725(7) | 0.7436(3) | 0.9141(8) | 5.3(2) |
| O64 | 0.7062(7) | 0.8164(3) | 0.427(1) | 5.9(2) |
| O65 | 0.8911(8) | 0.8598(2) | 0.535(1) | 6.1(2) |
| O67 | 0.3150(8) | 0.7090(3) | 1.184(1) | 6.4(2) |
| O68 | 0.5587(9) | 0.6986(3) | 1.377(1) | 6.6(2) |
| N52 | 0.4313(9) | 0.7713(3) | 1.271(1) | 4.9(2) |
| N55 | 0.4709(8) | 0.8265(3) | 1.0332(9) | 4.2(2) |
| N60 | 0.7555(8) | 0.7179(3) | 0.728(1) | 4.6(2) |
| N63 | 0.9491(8) | 0.7852(3) | 0.601(1) | 4.4(2) |
| N89 | 1.026(1) | 0.4719(3) | 0.711(1) | 6.0(3) |
| C51 | 0.442(1) | 0.7247(4) | 1.282(1) | 5.4(3) |
| C53 | 0.296(1) | 0.7996(4) | 1.141(1) | 5.1(3) |
| C54 | 0.3347(9) | 0.8159(3) | 0.989(1) | 4.1(3) |
| C56 | 0.519(1) | 0.8353(4) | 0.887(1) | 4.7(3) |
| C57 | 0.644(1) | 0.7959(4) | 0.886(1) | 4.5(3) |
| C58 | 0.587(1) | 0.7494(4) | 0.854(1) | 5.2(3) |

TABLE 3-continued

Table Of Fractional Parameters and Their
Estimated Standard Deviations for Form A

| Atom | x | y | z | B(A2) |
|---|---|---|---|---|
| C61 | 0.884(1) | 0.7334(4) | 0.766(1) | 4.2(3) |
| C62 | 0.914(1) | 0.7392(4) | 0.603(1) | 4.4(3) |
| C64 | 0.839(1) | 0.8196(4) | 0.513(1) | 4.6(3) |
| C66 | 0.785(2) | 0.8996(5) | 0.433(3) | 12.1(7) |
| C69 | 0.323(1) | 0.6588(4) | 1.202(2) | 8.8(5) |
| C70 | 0.237(1) | 0.8409(4) | 1.232(1) | 5.6(3) |
| C71 | 0.092(1) | 0.8701(5) | 1.080(2) | 7.6(4) |
| C72 | 0.352(1) | 0.8744(4) | 1.328(2) | 7.1(4) |
| C73 | 0.187(1) | 0.8195(6) | 1.362(1) | 8.9(4) |
| C74 | 0.570(1) | 0.8825(4) | 0.907(2) | 6.4(3) |
| C75 | 0.450(1) | 0.9206(4) | 0.919(1) | 6.3(3) |
| C76 | 0.296(2) | 0.9236(5) | 0.813(2) | 8.1(4) |
| C77 | 0.188(2) | 0.9614(6) | 0.826(2) | 11.2(5) |
| C78 | 0.244(2) | 0.9942(6) | 0.960(2) | 15.2(7) |
| C79 | 0.405(3) | 0.9935(6) | 1.062(2) | 13.9(7) |
| C80 | 0.504(2) | 0.9552(4) | 1.043(2) | 9.3(5) |
| C81 | 0.644(1) | 0.6672(4) | 0.832(2) | 6.2(3) |
| C82 | 0.762(1) | 0.6266(3) | 0.839(1) | 4.7(3) |
| C83 | 0.723(1) | 0.5934(4) | 0.696(2) | 6.1(3) |
| C84 | 0.822(1) | 0.5547(4) | 0.695(2) | 5.9(3) |
| C85 | 0.967(1) | 0.5478(4) | 0.828(1) | 5.0(3) |
| C86 | 1.009(1) | 0.5783(4) | 0.971(2) | 6.6(4) |
| C87 | 0.908(1) | 0.6184(4) | 0.971(2) | 6.4(4) |
| C88 | 1.076(1) | 0.5070(4) | 0.827(1) | 5.5(3) |
| C90 | 1.111(1) | 0.4326(4) | 0.690(2) | 7.4(4) |
| C91 | 1.258(2) | 0.4262(5) | 0.792(2) | 7.8(4) |
| C92 | 1.324(2) | 0.4578(5) | 0.918(2) | 8.7(5) |
| C93 | 1.230(1) | 0.4994(5) | 0.936(2) | 6.9(4) |
| C94 | 1.038(1) | 0.7005(4) | 0.584(1) | 4.8(3) |
| C95 | 1.196(1) | 0.7055(4) | 0.717(2) | 6.7(4) |
| C96 | 1.021(2) | 0.7049(5) | 0.392(2) | 8.9(4) |
| C97 | 0.998(1) | 0.6536(4) | 0.614(2) | 7.6(4) |
| N59 | 0.7084(8) | 0.7114(3) | 0.866(1) | 5.1(2) |
| H391 | 0.047 | 0.523 | 0.383 | 6.0* |
| H891 | 0.931 | 0.477 | 0.646 | 5.8* |
| H15' | 0.491 | 0.471 | 0.600 | 3.8* |
| H15" | 0.440 | 0.512 | 0.322 | 4.6* |

Most hydrogens have been omitted; only the hydrogens on N9 and the acid are included.

Anisotropically refined atoms are given in the form of the isotropic equivalent displacement parameter defined as: $(4/3)$ $*[a^2*B(1,1)+b^2*B(2,2)+c^2*B(3,3)+ab(\cos \gamma)*B(1,2) x+ac(\cos \beta)*B(1,3)+bc(\cos \alpha)*B(2,3)]$.

Form A is characterized by a differential scanning calorimetry thermogram having an endotherm typically within the range from about 165.6° C. to about 200.9° C. as shown in FIG. 3.

Form A is also characterized by a thermal gravimetric analysis curve having a negligible weight loss up to about 100 to 150° C.

The crystals produced by cubic crystallization where $H_2SO_4$ is added at an increasing rate according to the cubic equation described above were relatively larger and more well-defined, and had a narrower particle size range and fewer fines, than crystals obtained employing constant addition rate crystallization.

The filter cake obtained using the cubic crystallization technique was less compressible than that obtained using constant addition rate crystallization, which aided in effective cake deliquoring and washing and produced a homogeneous product.

TABLE 4

Carbon-13 SSNMR Chemical Shifts for Form A, measured
relative to TMS (tetramethyl silane)

δ/ppm

| |
|---|
| 26.9 |
| 27.5 |
| 33.9 |
| 37.7 |
| 49.2 |
| 53.5 |
| 62.7 |
| 63.3 |
| 66.0 |
| 69.2 |
| 69.5 |
| 122.6 |
| 123.7 |
| 125.3 |
| 126.1 |
| 127.6 |
| 128.5 |
| 129.4 |
| 131.1 |
| 134.4 |
| 138.8 |
| 139.7 |
| 140.6 |
| 143.2 |
| 143.9 |
| 149.9 |
| 150.3 |
| 153.9 |
| 159.3 |
| 172.0 |

Example 2

Atazanavir Bisulfate

Pattern C Material

Method A:

Form A crystals of atazanavir bisulfate (prepared as described in Example 1) (25.33 g) were suspended in 200 mL of water and the mixture was stirred mechanically to produce a thick gel which was dried.

The dried mixture was ground with a spatula to produce Pattern C material. A powder X-ray diffraction pattern of Pattern C material is shown in FIG. 6.

Method B:

Form A crystals of atazanavir bisulfate was wet granulated using a sufficient amount of water (about 40% w/w) in a suitable mixer-granulator. The wet mass was dried in an oven. The product was sized using a suitable screen. The x-ray diffraction pattern of the resultant product is consistent with Pattern C material as shown in FIG. 6.

Pattern C is characterized by the differential scanning calorimetry thermogram shown in FIG. 7 having an endotherm typically in the range from about 76.7 to about 96.6° C. and from about 156.8 to about 165.9° C.

Figure 8:
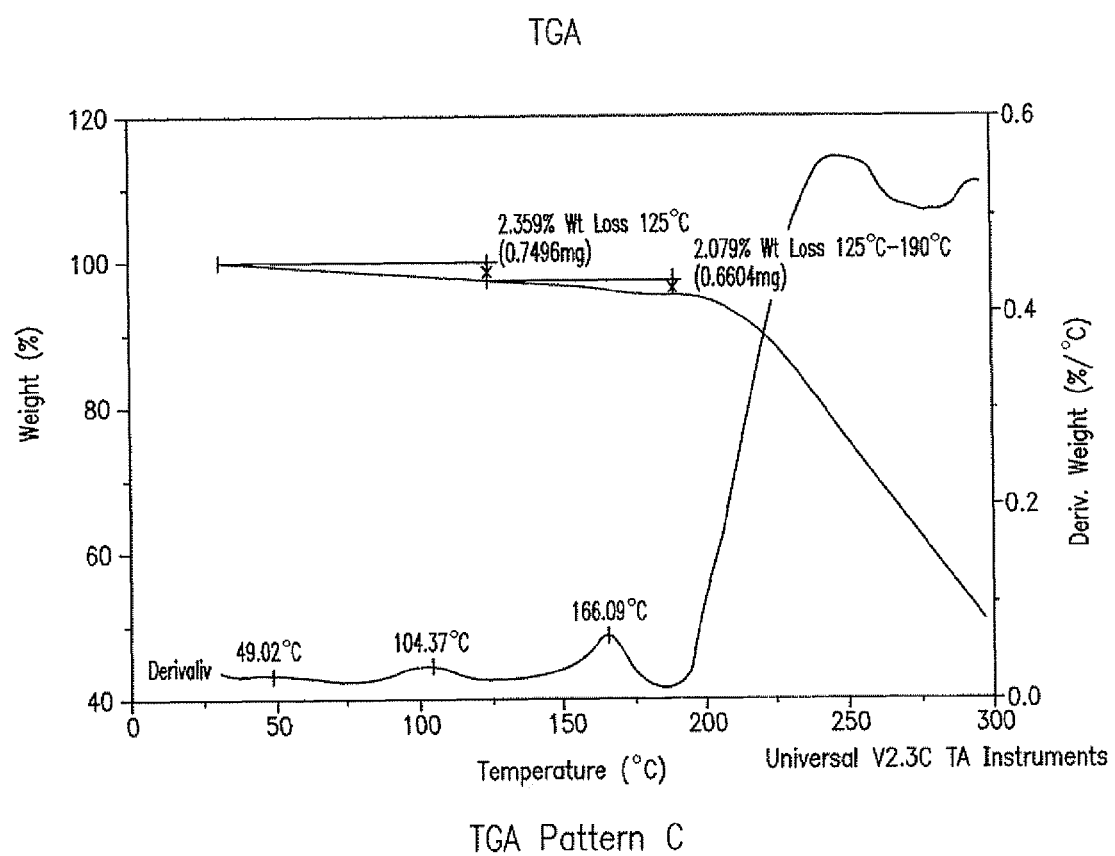
FIG. 8 shows a thermal gravimetric analysis curve of Pattern C.

Pattern C is also characterized by a thermal gravimetric analysis curve having a weight loss of about 2.4% at about 125° C. and about 4.4% at about 190° C. as shown in FIG. 8.

Example 3

Atazanavir Bisulfate Form E3

Triethanol Solvate

Atazanavir free base prepared as described in Example 1, Part C) (3.0 g, 4.26 mmol) was slurried in dry, 200 proof ethanol (20.25 mL, 6.75 mL/g of free base) in a 100 mL, 3-neck round-bottom flask fitted with a mechanical stirrer, temperature probe, and a pressure-equalizing liquid addition funnel.

Figure 9:
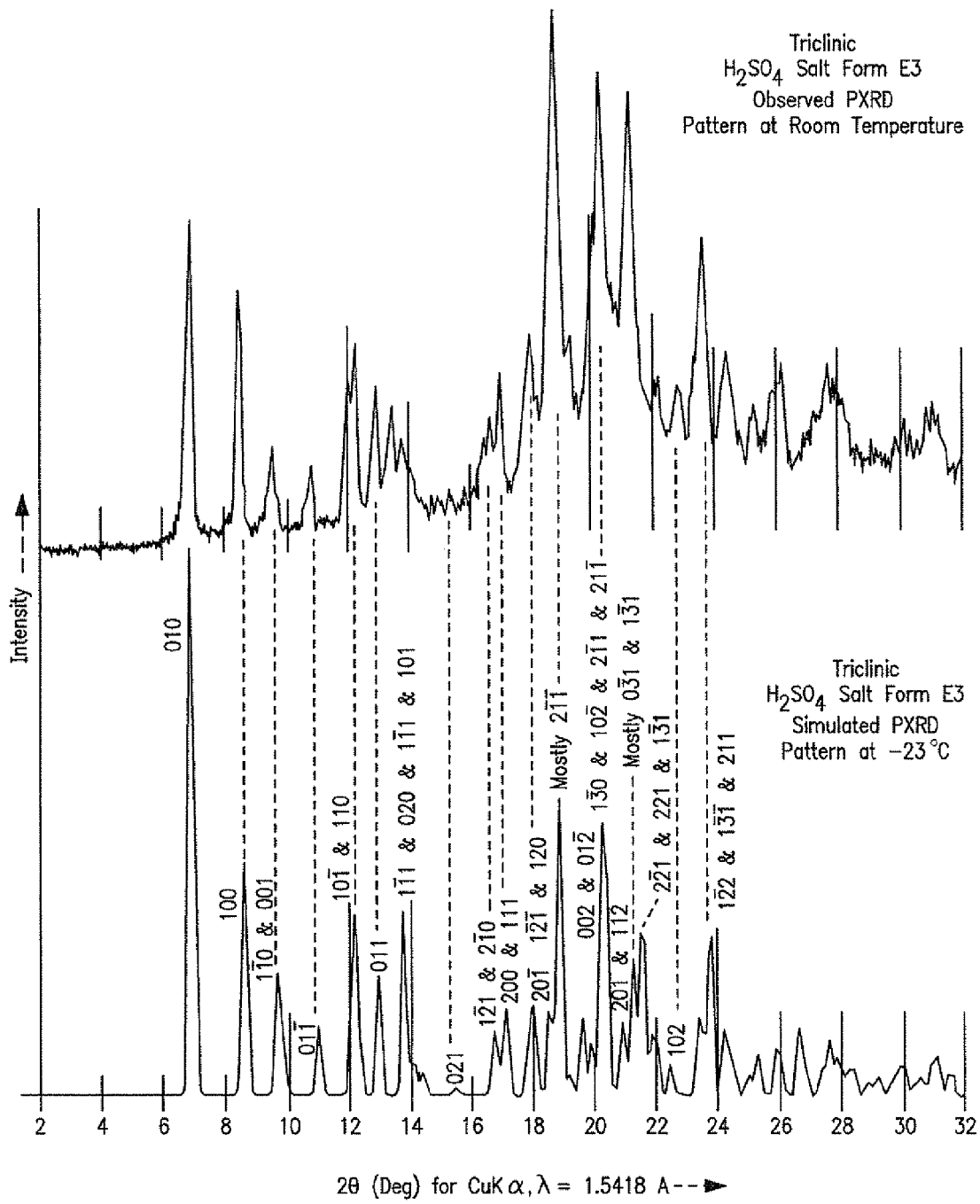
FIG. 9 shows calculated (simulated) (22° C.) and observed (experimental at room temperature) powder X-ray diffraction patterns (CuKα γ=1.5418 Å) of Form E3.
Figure 10:
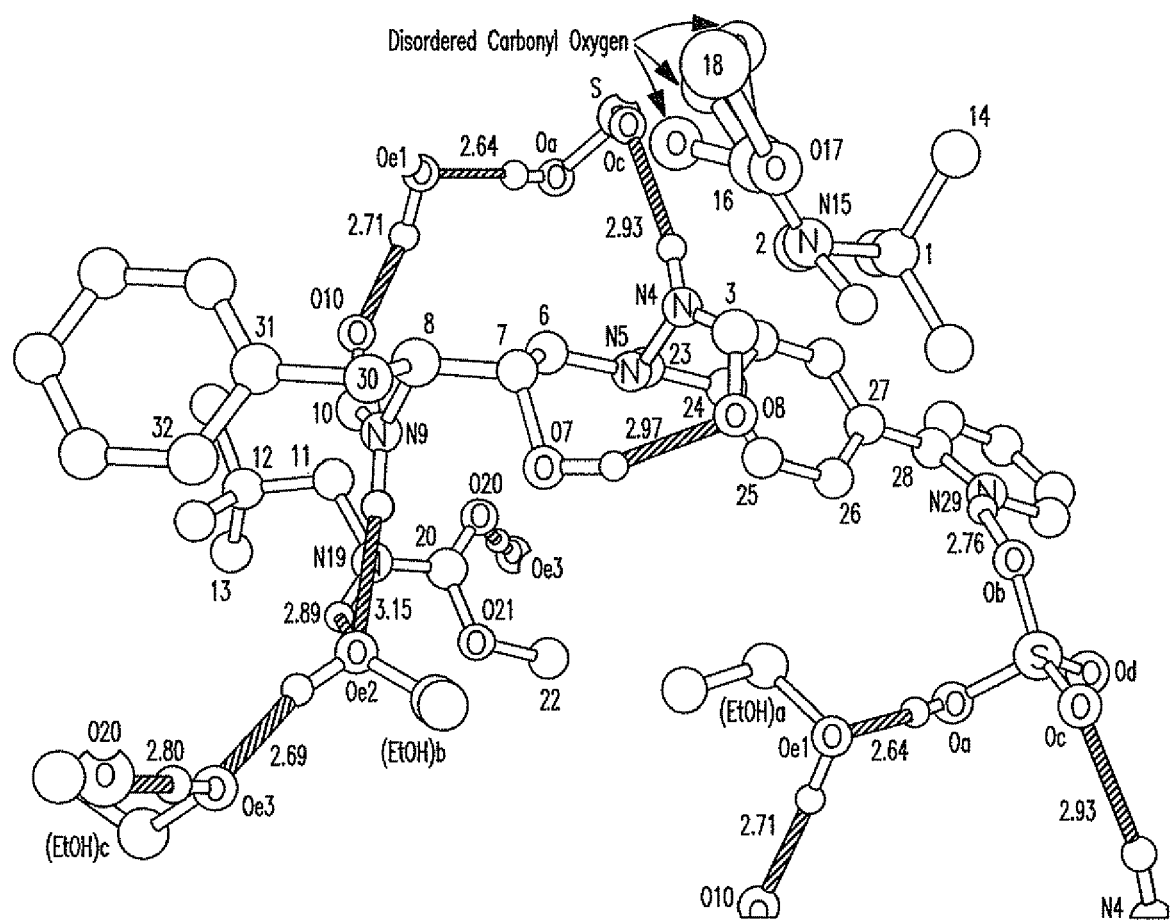
FIG. 10 shows the crystal structure of Form E3.

Concentrated $H_2SO_4$ (0.25 mL, 0.46 g, 4.69 mmol, 1.1 eq.) was added to the slurry of atazanavir free base which was maintained at 20-25° C. The resulting solution (KF of 0.2 to 1.0% water) was polish filtered (Whatman #1 paper), the filter rinsed with 2.25 mL of absolute ethanol and the rinse added to the filtered solution. The solution was heated to 37° C. and seeded with 10 mg of amorphous atazanavir bisulfate derived from Form E3 crystals (by exposing Form E3 crystals to ambient temperature), and the mixture was agitated for 15 min. Heptane (380 mL, 8.25 mL/g of free base) was added over 1 hour. The resulting crystallization mixture was agitated for 8 h at 15-25° C. Crystallized atazanavir bisulfate was filtered on a Büchner funnel. The product cake was washed with 184 mL (4 mL/g of free base) of 1:1 ethanol:heptane. The product cake was washed with 46 mL (1 mL/g of free base) of heptane. The resulting product was dried under vacuum at 40-50° C. until it had an LOD=0.97%. The yield of product was 47.7 g (0.0594 mol, 74.3 mol %) of atazanavir bisulfate Form E3 (triethanol solvate) with HPLC HI=100.0 (see FIGS. 9 and 10).

TABLE 5

Table of Crystallographic Data Form E3

| T° C. | a(Å) | b(Å) | c(Å) | α° | β° | γ° | V(Å$^3$) | Z' | sg | dcalc | R |
|---|---|---|---|---|---|---|---|---|---|---|---|
| −23 | 10.749(5) | 13.450(4) | 9.250(2) | 98.33(2) | 95.92(3) | 102.82(3) | 1277(2) | 1 | P1 | 1.223 | 0.06 |

T = temp(° C.) for the crystallographic data.
Z' = number of drug molecules per asymmetric unit

TABLE 6

Table of Fractional Parameters and Their Estimated Standard Deviations for Form E3

| Atom | x | y | z | B(A2) | Occupany if not equal to 1 |
|---|---|---|---|---|---|
| S99 | 0.5568(1) | 0.0760(1) | 0.5936(1) | 3.45(2) | |
| O1 | 0.4200(5) | 0.5541(4) | 0.8496(5) | 6.9(1) | |
| O2 | 0.2889(5) | 0.6016(4) | 1.0066(6) | 8.1(1) | |
| O4 | 0.7004(4) | 0.4509(3) | 1.0233(4) | 4.23(8) | |
| O8 | 0.2913(4) | 0.2932(3) | 1.1074(4) | 4.23(8) | |
| O12 | 0.1057(4) | 0.1088(3) | 0.9299(4) | 4.16(8) | |
| O15' | 0.329(1) | −0.0602(9) | 1.064(1) | 4.8(3)* | .3 |
| O15" | 0.324(2) | −0.156(1) | 1.003(2) | 3.2(3)* | .17 |
| O15 | 0.3312(7) | −0.1150(6) | 1.0380(8) | 4.9(1)* | .53 |
| O16 | 0.1810(5) | −0.1433(3) | 1.1819(4) | 5.7(1) | |
| O86 | 0.391(1) | 0.6646(7) | 0.6196(9) | 11.5(4) | |
| O89 | 0.3714(7) | 0.5646(5) | 0.3408(6) | 6.5(2) | |
| O90 | 0.7502(4) | 0.2721(3) | 0.8957(5) | 4.99(9) | |
| O95 | 0.4984(5) | 0.0446(3) | 0.7188(4) | 4.50(8) | |
| O96 | 0.6644(4) | 0.0315(3) | 0.5660(4) | 4.83(8) | |
| O97 | 0.4651(4) | 0.0667(3) | 0.4636(4) | 5.08(9) | |
| O98 | 0.6112(5) | 0.1957(3) | 0.6332(5) | 5.9(1) | |
| N2 | 0.4938(5) | 0.6229(3) | 1.0921(5) | 4.8(1) | |
| N5 | 0.5365(4) | 0.4385(3) | 1.1609(4) | 3.16(8) | |
| N10 | 0.2952(4) | 0.2239(3) | 0.8056(4) | 3.17(8) | |
| N11 | 0.2716(4) | 0.1163(3) | 0.7961(4) | 3.08(8) | |
| N14 | 0.1336(5) | −0.0874(4) | 0.9743(5) | 4.9(1) | |
| N38 | −0.2764(4) | 0.0574(3) | 0.2878(4) | 3.24(8) | |
| C1 | 0.4011(6) | 0.5893(4) | 0.9712(7) | 5.3(1) | |
| C3 | 0.6225(5) | 0.6026(4) | 1.0813(5) | 3.9(1) | |
| C4 | 0.6231(5) | 0.4896(3) | 1.0873(5) | 3.19(9) | |
| C6 | 0.5220(5) | 0.3284(3) | 1.1691(5) | 3.14(9) | |
| C8 | 0.4026(5) | 0.2632(3) | 1.0653(5) | 3.21(9) | |
| C9 | 0.4165(5) | 0.2747(4) | 0.9050(5) | 3.6(1) | |
| C12 | 0.1740(5) | 0.0661(4) | 0.8596(5) | 3.4(1) | |
| C13 | 0.1592(5) | −0.0523(4) | 0.8367(5) | 3.8(1) | |
| C15 | 0.2248(6) | −0.1124(5) | 1.0627(6) | 4.6(1) | |
| C17 | 0.2720(9) | −0.1732(6) | 1.2842(7) | 7.3(2) | |
| C18 | 0.1818(9) | 0.5715(9) | 0.894(1) | 11.2(3) | |
| C19 | 0.7292(7) | 0.6818(4) | 1.1928(7) | 5.8(2) | |
| C20 | 0.725(1) | 0.7914(6) | 1.169(1) | 10.7(3) | |
| C21 | 0.8613(9) | 0.6645(8) | 1.165(1) | 10.5(3) | |
| C22 | 0.710(1) | 0.6694(7) | 1.3507(8) | 10.2(3) | |
| C23 | 0.5158(5) | 0.3135(4) | 1.3298(5) | 3.8(1) | |
| C24 | 0.6305(6) | 0.3765(4) | 1.4359(5) | 4.0(1) | |
| C25 | 0.7519(7) | 0.3708(6) | 1.4192(7) | 6.1(2) | |
| C26 | 0.8581(7) | 0.4279(7) | 1.5213(9) | 7.9(2) | |
| C27 | 0.8398(8) | 0.4935(6) | 1.6375(8) | 8.6(2) | |
| C28 | 0.715(1) | 0.5002(6) | 1.6576(7) | 8.0(2) | |
| C29 | 0.6112(8) | 0.4430(5) | 1.5589(6) | 6.0(2) | |
| C30 | 0.3043(5) | 0.2519(4) | 0.6582(5) | 3.6(1) | |
| C31 | 0.1813(5) | 0.2051(4) | 0.5532(5) | 3.4(1) | |
| C32 | 0.0645(5) | 0.2123(4) | 0.5934(5) | 3.9(1) | |
| C33 | −0.0489(5) | 0.1725(4) | 0.4957(5) | 3.8(1) | |
| C34 | −0.0441(5) | 0.1243(4) | 0.3503(5) | 3.16(9) | |
| C35 | 0.0756(5) | 0.1176(4) | 0.3097(5) | 3.9(1) | |
| C36 | 0.1867(5) | 0.1568(4) | 0.4095(5) | 3.9(1) | |
| C37 | −0.1615(5) | 0.0853(4) | 0.2417(4) | 3.11(9) | |
| C39 | −0.3885(5) | 0.0247(4) | 0.1969(5) | 3.9(1) | |
| C40 | −0.3891(5) | 0.0200(4) | 0.0470(5) | 4.2(1) | |
| C41 | −0.2737(6) | 0.0469(4) | −0.0057(5) | 4.1(1) | |
| C42 | −0.1596(5) | 0.0781(4) | 0.0890(5) | 3.7(1) | |
| C43 | 0.0488(6) | −0.1114(4) | 0.7094(6) | 4.6(1) | |
| C44 | −0.0819(7) | −0.0958(6) | 0.7378(9) | 6.8(2) | |
| C45 | 0.0496(9) | −0.2266(5) | 0.6929(9) | 7.8(2) | |
| C46 | 0.0797(8) | −0.0738(5) | 0.5667(7) | 6.2(2) | |
| C84 | 0.569(1) | 0.7880(9) | 0.725(1) | 6.3(3) | |
| C85 | 0.448(1) | 0.7726(9) | 0.673(2) | 8.4(4) | |
| C87 | 0.204(1) | 0.449(1) | 0.405(2) | 10.6(4) | |
| C88 | 0.240(1) | 0.517(1) | 0.316(1) | 8.6(3) | |
| C91 | 0.8826(7) | 0.2919(5) | 0.8896(8) | 5.8(2) | |
| C92 | 0.9613(7) | 0.3439(6) | 1.035(1) | 7.8(2) | |
| H381 | −0.275 | 0.053 | 0.403 | 3.2 | |
| H891 | 0.397 | 0.602 | 0.446 | 6.6 | |
| H981 | 0.658 | 0.219 | 0.717 | 6.6 | |

Most hydrogens have been omitted; only the hydrogens on N9 and the acid are included.

Anisotropically refined atoms are given in the form of the isotropic equivalent displacement parameter defined as: (4/3) *[a2*B(1,1)+b2*B(2,2)+c2*B(3,3)+ab(cos gamma)*B(1,2) x+ac(cos beta)*B(1,3)+bc(cos alpha)*B(2,3)].

Figure 11:
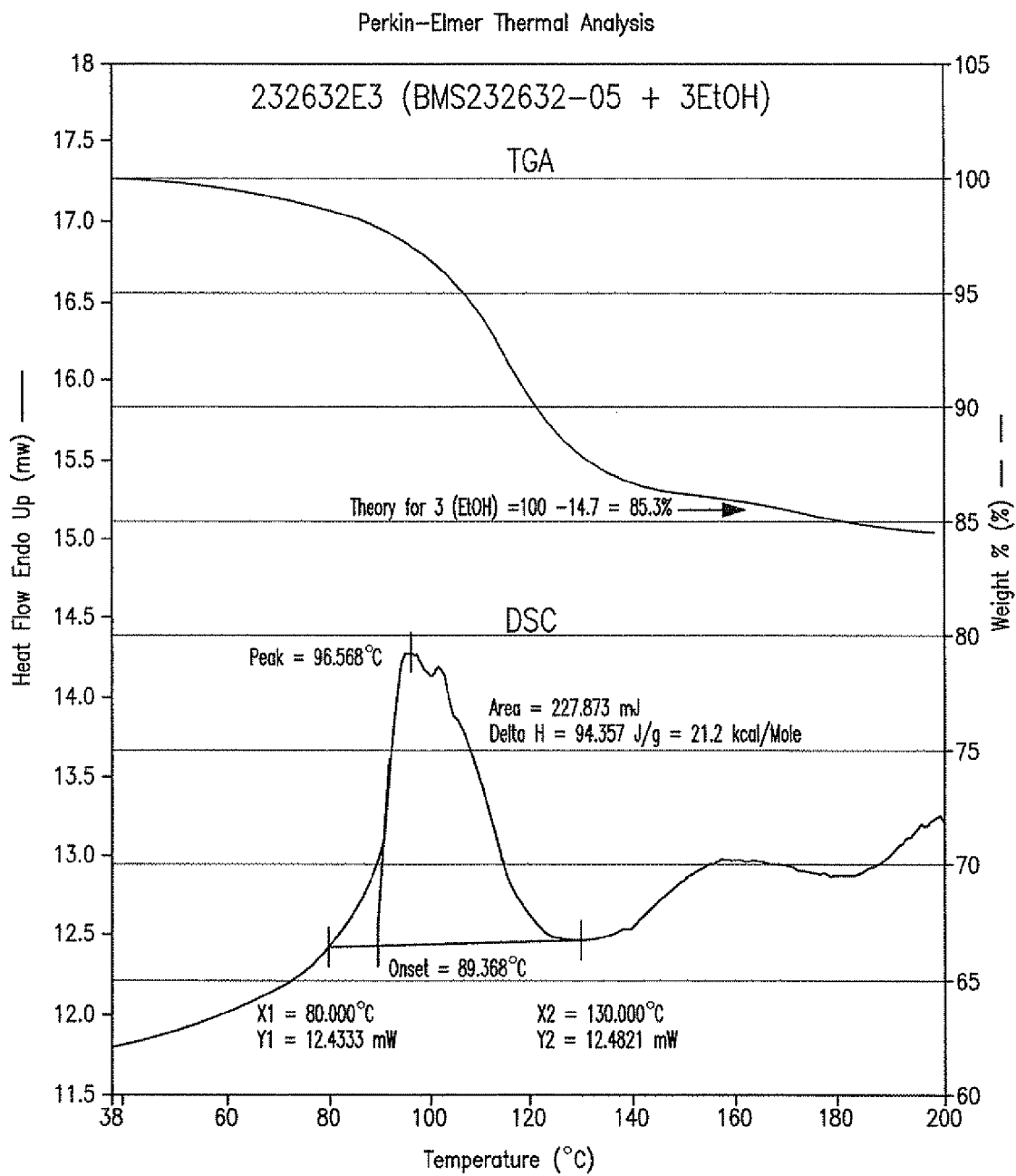
FIG. 11 shows a differential scanning calorimetry (DSC) thermogram of Form E3, and a thermal gravimetric analysis curve of Form E3.

Form E3 is characterized by the differential scanning calorimetry thermogram having an endotherm typically within the range from about 89.4 to about 96.6 as shown in FIG. 11.

Form E3 is also characterized by a thermal gravimetric analysis curve having a weight loss of about 14.7% at about 150° C. as shown in FIG. 11.

Example 4

Atazanavir bisulfate Pattern C capsule formulations having the following compositions were prepared as described below.

| Ingredient | Stock Granulation[a] (% w/w) | 50-mg Capsule (mg/Capsule) | 100-mg Capsule (mg/Capsule) | 200-mg Capsule (mg/Capsule) |
|---|---|---|---|---|
| Atazanavir bisulfate | 63.2 | 56.84[b] | 113.67[b] | 227.34[b] |
| Lactose, Monohydrate, NF | 30.4 | 27.33[c] | 54.69[c] | 109.35[c] |
| Crospovidone, NF | 6.0 | 5.39 | 10.79 | 21.58 |
| Magnesium Stearate, NF | 0.4 | 0.36[d] | 0.72[d] | 1.44[d] |
| Purified Water, USP or Water for Injection, USP | q.s.[e] | q.s.[e] | q.s.[e] | q.s.[e] |
| Size #4 Capsule | — | 1 Each | — | — |
| Size #2 Capsule | — | — | 1 Each | — |
| Size #0 Capsule | — | — | — | 1 Each |
| Total Fill Weight | 100.0 | 89.9 | 179.9 | 359.7 |

[a]Atazanavir bisulfate Stock Granulation for Capsules (55.5% w/w as the Free Base) was used to manufacture the 50 mg, 100 mg, and 200 mg capsules.
[b]This amount is expressed in terms of atazanavir bisulfate at 100% potency, and is equal to 55.5% w/w as the Free Base.
[c]The amount of lactose, hydrous will vary depending on the purity of atazanavir bisulfate and the amount of magnesium stearate used.
[d]The amount of magnesium stearate used may vary from 0.4% w/w to 0.8% w/w.
[e]This is used for processing only and is removed by drying.

The stock granulation of atazanavir bisulfate was prepared as follows, in which Pattern C material was formed.

Atazanavir bisulfate Form A, lactose hydrous, and a portion of crospovidone (3% by weight of total crospovidone present) were mixed in a planetary mixer. The resulting blend was wet granulated with purified water to convert Form A to Pattern C material. The wet granulation was dried in a tray dryer and was sized using a hammer mill. The remaining crospovidone was added to the milled granulation and the mixture was mixed in a PK V-blender. Magnesium stearate was added and the mixture was mixed until a substantially uniform stock granulation was formed.

The appropriate weight of stock granulations were filled into capsules to produce 50 mg, 100 mg and 200 mg capsules containing atazanavir bisulfate.

Example 5

Atazanavir bisulfate Form A material powder for oral use formulation having the following composition is prepared as described below.

| Ingredients | Amount (% w/w) |
|---|---|
| Atazanavir Bisulfate Form A | 3.79 |
| Aspartame, NF | 10.00 |
| Sucrose, NF | 81.21 |
| Orange vanilla flavor | 5.00 |

Atazanavir bisulfate Form A is mixed with aspartame, orange vanilla flavor and sucrose in a suitable mixer. The mixture is milled using a hammer mill, followed by a second mixing operation to obtain a uniform mixture. The product is filled into high density polyethylene bottles.

What is claimed is:

1. A process for preparing atazanavir bisulfate Pattern C material, which comprises (a) suspending crystals of Form A atazanavir bisulfate in water and drying the suspension to form Pattern C material; or
 (b) subjecting crystals of Form A atazanavir bisulfate to high relative humidity of greater than 95% RH for at least 24 hours to form Pattern C material; or
 (c) mixing Form A crystals with one or more formulating excipients and wet granulating the resulting mixture to directly form Pattern C material in admixture with the excipients.

2. A process for preparing atazanavir bisulfate

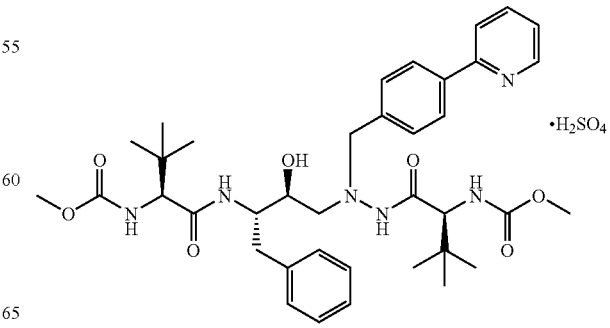

in the form of Pattern C material, which comprises preparing a triamine salt of the structure

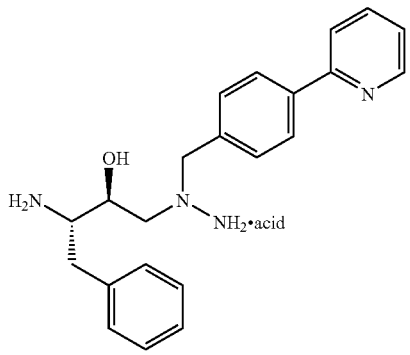

and without isolating the triamine salt, reacting the triamine salt with an active ester of an acid of the structure

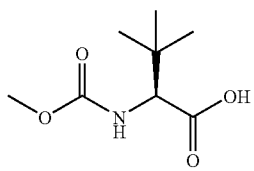

and a base in the presence of an organic solvent to form a solution of the atazanavir free base of the structure

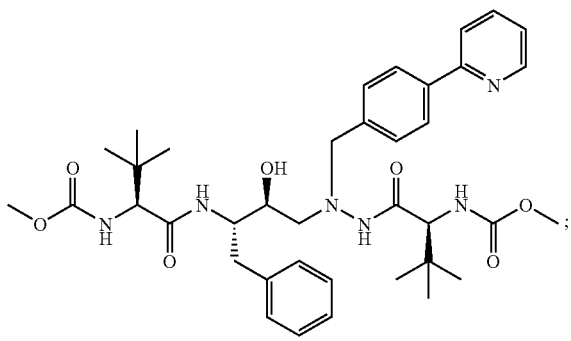

(a) reacting a solution of atazanavir free base in an organic solvent, in which the bisulfate salt of atazanavir is substantially insoluble, with a first portion of concentrated sulfuric acid in an amount to react with from about 5 to about 15% by weight of the atazanavir free base;
(b) adding seeds of Form A crystals of atazanavir bisulfate to the reaction mixture;
(c) as crystals of atazanavir bisulfate form, adding additional concentrated sulfuric acid in multiple stages at an increasing rate to effect formation of atazanavir bisulfate Form A crystals;
(d) suspending crystals of Form A atazanavir bisulfate in water and drying the suspension to form Pattern C material; or
(e) subjecting crystals of Form A atazanavir bisulfate to high relative humidity of greater than 95% RH for at least 24 hours to form Pattern C material; or
(f) wet granulating Form A atazanavir bisulfate and drying the wet granulation to form Pattern C material; or
(g) mixing Form A crystals with one or more formulating excipients and wet granulating the resulting mixture to directly form Pattern C material in admixture with the excipients.

3. The process as defined in claim 2 where the triamine salt is the hydrochloride salt

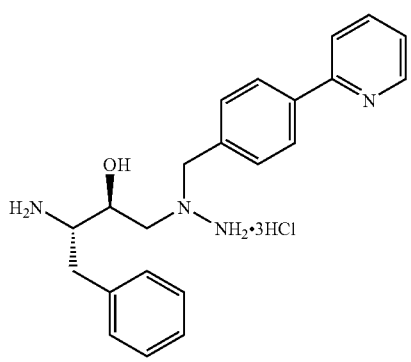

and the active ester of the acid has the structure

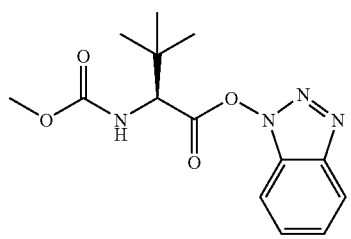

and the base is an alkali metal hydroxide, an alkaline earth metal hydroxide, an alkali metal carbonate, an alkaline earth metal carbonate, an alkali metal phosphate, an alkaline earth metal phosphate or an organic base, and the triamine salt and the active ester are reacted at a temperature within the range from about 30 to about 40° C.

4. The process, as defined in claim 3 wherein the base is NaOH, KOH, Mg(OH)$_2$, K$_2$HPO$_4$, MgCO$_3$, Na$_2$CO$_3$, K$_2$CO$_3$, triethylamine, diisopropylethylamine or N-methylmorpholine and the organic solvent is methylene chloride, ethyl acetate, dichloroethane, tetrahydrofuran, acetonitrile or N,N-dimethylformamide.

5. The process as defined in claim 2 wherein the free base is converted to the corresponding bisulfate salt Form A by treating a solution of free base in methylene chloride with N-methylpyrrolidone and acetone, heating the above mixture to remove methylene chloride, seeding the mixture of free base, acetone and N-methylpyrrolidone with crystals of atazanavir bisulfate and adding sulfuric acid at an increasing rate to the above mixture to form the bisulfate salt of the free base in the form of Form A crystals.

6. The process as defined in claim 5 wherein the sulfuric acid is added at an increasing rate according to the following equation $$V_{time} = V_{total} \times \left(\frac{time}{time_{total}}\right)^3$$

where
- $V_{time}$=Volume of sulfuric acid added during elapsed time period
- $V_{total}$=Total volume of acid representing the 90% charge
- time=Elapsed time in crystallization
- $time_{total}$=Total crystallization time or total time for acid charging.

7. A process for preparing atazanavir bisulfate Pattern C material, which comprises
   (a) reacting a solution of atazanavir free base in an organic solvent, in which the bisulfate salt of atazanavir is substantially insoluble, with a first portion of concentrated sulfuric acid in an amount to react with from about 5 to about 15% by weight of the atazanavir free base;
   (b) adding seeds of Form A crystals of atazanavir bisulfate to the reaction mixture;
   (c) as Form A crystals of atazanavir bisulfate form, adding additional concentrated sulfuric acid in multiple stages at an increasing rate to effect formation of atazanavir bisulfate Form A crystals;
   (d) suspending crystals of Form A atazanavir bisulfate in water and drying the suspension to form Pattern C material; or
   (e) subjecting crystals of Form A atazanavir bisulfate to high relative humidity of greater than 95% RH for at least 24 hours to form Pattern C material; or
   (f) wet granulating Form A atazanavir bisulfate and drying the wet granulation to form Pattern C material; or
   (g) mixing Form A crystals with one or more formulating excipients and wet granulating the resulting mixture to directly form Pattern C material in admixture with the excipients.

8. The process as defined in claim 7 wherein the solution of atazanavir free base is initially reacted with from about 5 to less than about 12% by weight of the total amount of sulfuric acid employed.

9. The process as defined in claim 7 wherein the solution of atazanavir free base is initially reacted with from about 8 to about 12% by weight of the total amount of sulfuric acid employed.

10. The process as defined in claim 7 wherein the reaction mixture of atazanavir free base and sulfuric acid is seeded with from about 0.1 to about 80 weight % of Form A crystals based on the weight of atazanavir free base.

11. The process as defined in claim 7 wherein the sulfuric acid is added at an increasing rate according to the following equation $$V_{time} = V_{total} \times \left(\frac{time}{time_{total}}\right)^3$$

where
- $V_{time}$=Volume of sulfuric acid added during elapsed time period
- $V_{total}$=Total volume of acid representing the 90% charge
- time=Elapsed time in crystallization
- $time_{total}$=Total crystallization time or total time for acid charging.

12. The process as defined in claim 1 wherein the sulfuric acid is added at an increasing rate according to the following equation $$V_{time} = V_{total} \times \left(\frac{time}{time_{total}}\right)^3$$

where
- $V_{time}$=Volume of sulfuric acid added during elapsed time period
- $V_{total}$=Total volume of acid representing the 90% charge
- time=Elapsed time in crystallization
- $time_{total}$=Total crystallization time or total time for acid charging.

* * * * *